US009243891B2

(12) United States Patent
Bobasheva et al.

(10) Patent No.: US 9,243,891 B2
(45) Date of Patent: Jan. 26, 2016

(54) METHODS AND APPARATUS FOR ACQUIRING PHYSICAL MEASUREMENTS RELATING TO A VESSEL AND A SHAFT WITHIN A VESSEL

(75) Inventors: Anna Bobasheva, Raleigh, NC (US); David Moody, Cary, NC (US); Deon Smit, Cary, NC (US); Francisco Alonso, Cary, NC (US); Jeffrey Kuhn, Durham, NC (US); Jeremy Fetvedt, Raleigh, NC (US); John W. Taylor, Loveland, CO (US)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 1245 days.

(21) Appl. No.: 12/905,806

(22) Filed: Oct. 15, 2010

(65) Prior Publication Data

US 2012/0095723 A1    Apr. 19, 2012

(51) Int. Cl.

| | |
|---|---|
| *G01P 3/32* | (2006.01) |
| *G01P 3/26* | (2006.01) |
| *G01P 3/44* | (2006.01) |
| *G01P 3/486* | (2006.01) |
| *G01B 11/00* | (2006.01) |
| *G01B 11/08* | (2006.01) |
| *G01B 11/14* | (2006.01) |
| *G01B 11/27* | (2006.01) |
| *G01P 3/487* | (2006.01) |
| *G01N 13/00* | (2006.01) |

(52) U.S. Cl.
CPC ............. *G01B 11/002* (2013.01); *G01B 11/08* (2013.01); *G01B 11/14* (2013.01); *G01B 11/272* (2013.01); *G01P 3/487* (2013.01); *G01N 2013/006* (2013.01)

(58) Field of Classification Search
CPC ........................................................ G01N 3/00
USPC ............. 702/20, 49, 142, 145, 149, 150, 151, 702/154, 179; 33/520; 73/61.45; 177/208; 356/4.01; 600/407
See application file for complete search history.

(56) References Cited

U.S. PATENT DOCUMENTS

| | | | | |
|---|---|---|---|---|
| 3,964,296 | A | * | 6/1976 | Matzuk ............................ 73/607 |
| 4,062,415 | A | * | 12/1977 | Miller ............................. 177/208 |
| 4,848,157 | A | * | 7/1989 | Kobayashi .................. 73/514.33 |
| 4,852,396 | A | * | 8/1989 | Tavlarides et al. ........... 73/61.45 |
| 5,983,515 | A | | 11/1999 | Brinker et al. |
| 6,434,847 | B1 | * | 8/2002 | Duckett et al. .................. 33/520 |
| 6,474,182 | B2 | | 11/2002 | Duckett et al. |
| 6,546,821 | B2 | | 4/2003 | Duckett et al. |
| 7,047,809 | B2 | * | 5/2006 | Cobb .............................. 73/599 |
| 7,330,242 | B2 | * | 2/2008 | Reichert et al. ............. 356/4.01 |
| 8,214,010 | B2 | * | 7/2012 | Courtney et al. ............. 600/407 |
| 2003/0086823 | A1 | * | 5/2003 | Fernando et al. ............... 422/81 |

* cited by examiner

*Primary Examiner* — John Breene
*Assistant Examiner* — Felix Suarez

(57) ABSTRACT

An apparatus is used for determining at least one parameter relating to an elongate member disposed within a vessel. The apparatus includes at least one measurement unit having a light emitting component and a corresponding light receiving component. The light receiving component is positioned apart from the light emitting component such that the elongate member is positionable between the light emitting component and the light receiving component. Additionally, the light emitting component is adapted to emit light towards the light receiving component, and the light receiving component is adapted to generate a signal corresponding to the light received from the light emitting component. A method for determining at least one parameter relating to the elongate member disposed within the vessel is also provided.

20 Claims, 23 Drawing Sheets

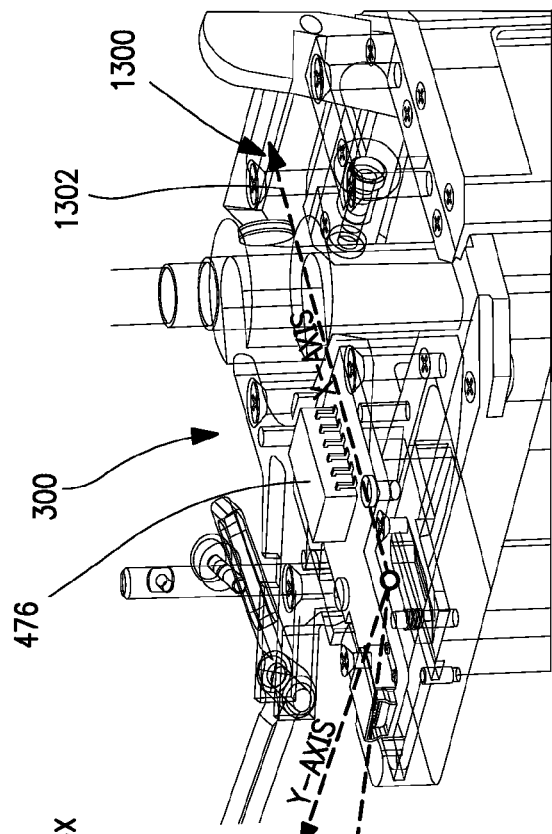
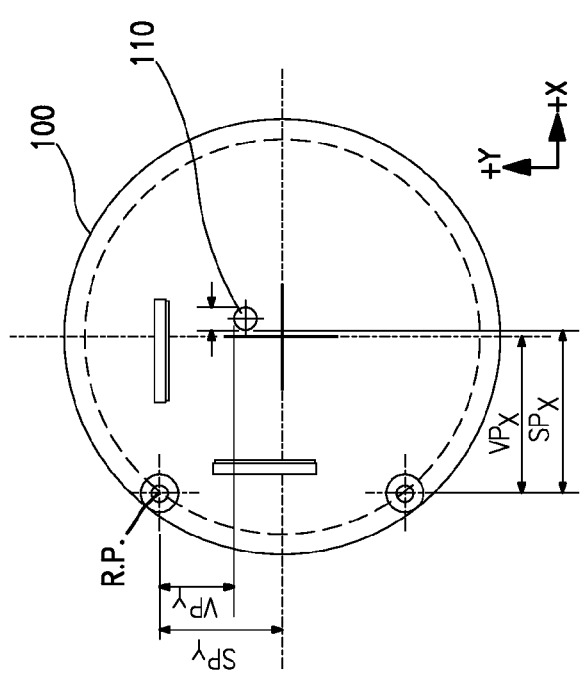
FIG. 12
FIG. 13

METHODS AND APPARATUS FOR ACQUIRING PHYSICAL MEASUREMENTS RELATING TO A VESSEL AND A SHAFT WITHIN A VESSEL

FIELD OF THE INVENTION

The present invention generally relates to measurement of physical parameters relating to a vessel and a shaft within a vessel including, for example, the amount by which the shaft is offset from the center of the vessel, the diameter of the shaft, the amount by which the shaft and vessel are angularly offset from a vertical axis, the distance of the shaft from the bottom of the vessel, and the rotations-per-minute and wobble of the shaft during operation. More particularly, the present invention relates to such precise measurement physical measurements in vessels employed in dissolution testing systems.

BACKGROUND OF THE INVENTION

In the pharmaceutical industry, dissolution testing and analysis is required to be performed on samples taken from batches of tablets or capsules manufactured by pharmaceutical companies in order to assess efficacy and other properties. Dissolution analysis by automated means has become popular for increasing throughput and improving accuracy, precision, reliability, and reproducibility. Automation also relieves the tedium of manually performing a variety of requisite procedures, including: handling and delivering dosage units such as capsules and tablets; monitoring dissolution system parameters; manipulating the shafts carrying the agitation paddles or sample baskets; recording, displaying and printing accumulated data and test results; and cleaning and filtering the vessels employed in such procedures.

Despite the benefits accruing from automation, validation of the procedures employed in dissolution testing and analysis remains a critical consideration. A typical dissolution test requires, among other things, that a rotatable shaft equipped with a paddle or basket be properly positioned in the center of and properly located a specified distance from the bottom of, a dissolution test vessel prior to conducting the test. The USP has promulgated guidelines for the pharmaceutical industry which are enforced by the FDA. Under USP 24, General Chapters, Dissolution (711), the shaft must be positioned such that its centerline is not more than 2 mm at any point from the vertical axis of the vessel, and such that the paddle or basket (typically mounted to the lower end of the shaft) be positioned at 25 mm±2 mm from the bottom of the vessel. Similar guidelines specify standards relating to the diameter of the shaft, the angular offset of the shaft and the vessel from a vertical axis, the wobble of the shaft and shaft basket during operation, and the rotations-per-minute (RPMs) of the shaft during operation.

Systems and methods have been developed to automatically acquire the physical measurements relating to the vessel and the shaft, which improved upon various hand-held devices such as rulers, machinist calipers and micrometers, and pass/fail fixtures. These systems and methods reduced the amount of manual handling and reduced reliance on sight and feel when acquiring physical measurements. However, such systems may require attachment of the measurement device to the shaft. The attachment of the measurement device to the shaft may apply force to the shaft potentially disturbing the position of the shaft within the vessel. Moreover, these known systems may require an operator to take multiple readings and reposition the measurement device within the vessel for subsequent readings. This manipulation of the measurement device may further disturb the position of the shaft within the vessel. There accordingly exists a need for an improved apparatus and improved methods for acquiring physical parameters relating to a vessel and a shaft within a vessel of a dissolution apparatus.

SUMMARY OF THE INVENTION

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one implementation, an apparatus is used for determining at least one parameter relating to an elongate member disposed within a vessel. The apparatus includes at least one measurement unit having a light emitting component and a corresponding light receiving component. The light receiving component is positioned apart from the light emitting component such that the elongate member is positionable between the light emitting component and the light receiving component. Additionally, the light emitting component is adapted to emit light towards the light receiving component, and the light receiving component is adapted to generate a signal corresponding to the light received from the light emitting component.

According to another implementation, a method is used for determining at least one parameter relating to an elongate member disposed within a vessel. The method includes the step of obtaining measurements relating to the elongate member disposed within the vessel with an apparatus positioned within a bore of the vessel. The apparatus is spaced apart from the elongate member. Additionally, the method includes the step of determining at least one parameter relating to the elongate member based on the measurements obtained from the apparatus.

Other devices, apparatus, systems, methods, features and advantages of the invention will be or will become apparent to one with skill in the art upon examination of the following figures and detailed description. It is intended that all such additional systems, methods, features, and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

FIG. 12 is a top schematic view of a vessel and a shaft illustrating the measurements that may be used to calculate the shaft offset from the center of the vessel.

FIG. 13 is a perspective schematic view of the measurement device disposed within a vessel illustrating the measurements that may be used to calculate the verticality of the vessel.

DETAILED DESCRIPTION OF THE INVENTION

Figure 1:
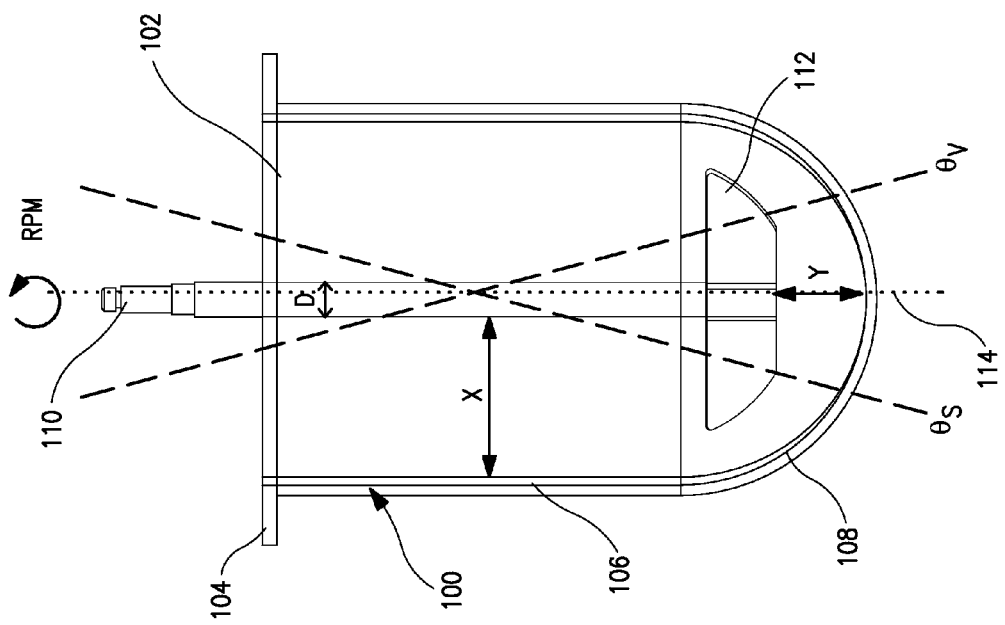
FIG. 1 is a cross-sectional view of a paddle shaft installed in a vessel.

FIG. 1 illustrates a typical vessel 100 that may be employed in a dissolution apparatus. The vessel 100 has an open upper end 102 surrounded by a horizontal rim 104, a lateral side region 106, and a hemispherical lower end region 108. An elongate member or a shaft 110 having an agitator such as a paddle 112 or basket (not shown) is inserted into the vessel 100. The parameters relevant to the vessel 100 and shaft 110 as depicted in FIG. 1 include: the location of the shaft 110 from the central vertical axis of the vessel 100 determined by shaft distance X; the height of the shaft 110 as determined by distance Y from the bottom of the vessel 100 to the bottom of the paddle 112, or other agitator; the diameter of the shaft 110 as determined by dimension D; the angular position of the shaft 110 relative to the central vertical axis 114 of the vessel as determined by angle $\Theta_S$; the angular position of the vessel 100 from the central vertical axis 114 of the vessel as determined by angle $\Theta_V$; the rotational speed of the shaft 110 during an operative mode, such as when the shaft 110 is rotating; and the deviation (wobble) from the central vertical axis 114 of the vessel of the shaft 110 or the agitator 112 during an operative mode.

Figure 2:
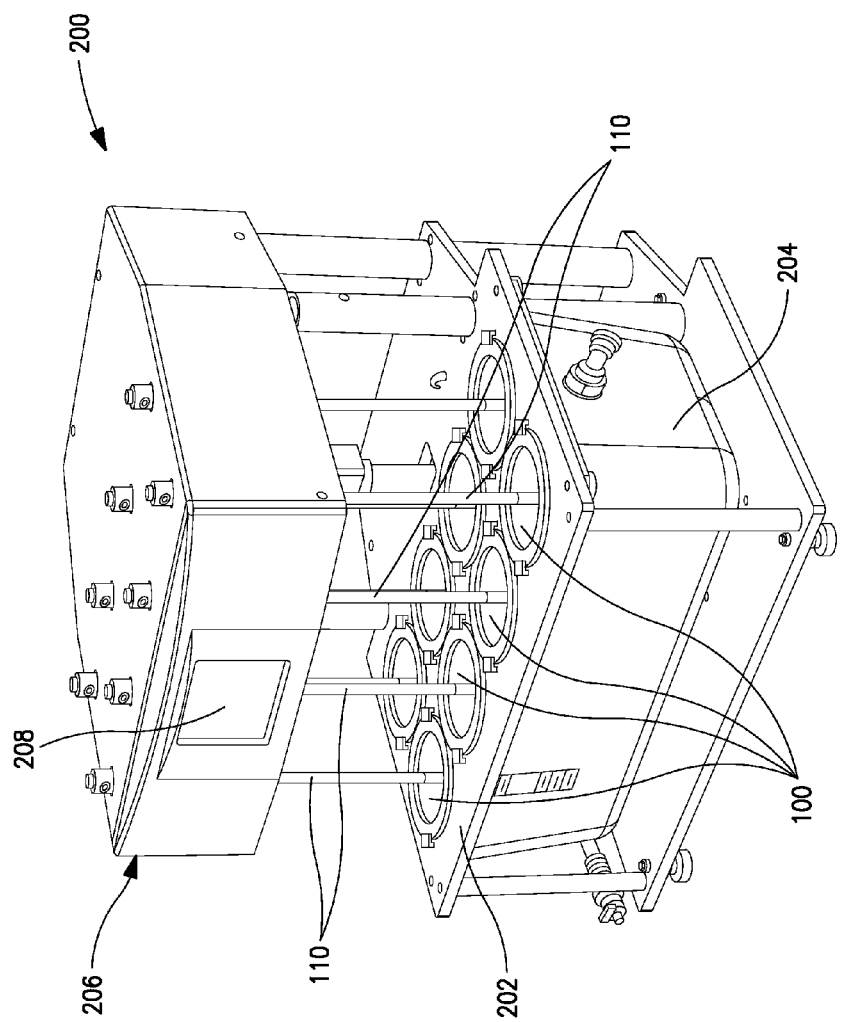
FIG. 2 is a perspective view of a dissolution apparatus.

FIG. 2 illustrates an example dissolution apparatus 200 for multiple vessels 100. In the example testing station 200 shown in FIG. 2, eight total vessels 100 are arranged in two rows of four vessels each. The vessels 100 are mounted in a vessel plate 202 of the dissolution apparatus 200. Each vessel 100 may be centered and locked into position on the vessel plate 202 with the aid of a vessel centering ring (not shown), magnetic coupling, or other mechanical mechanism. Other components of the dissolution apparatus 200 include: a water bath 204 to control the temperature of the vessels 100 and a programmable control module 206. The control module 206 may include peripheral elements such as a touch-sensitive LCD control and display screen 208. The control module 206 may house multiple spindle motors or alternately a single motor with a belt drive attached to spindle pulleys corresponding to each vessel 100 mounted in the vessel plate 202 of the dissolution apparatus 200. A shaft 110 may be coupled to a corresponding spindle motor via a suitable coupling means such as a chuck (not shown) for example.

Figure 3A:
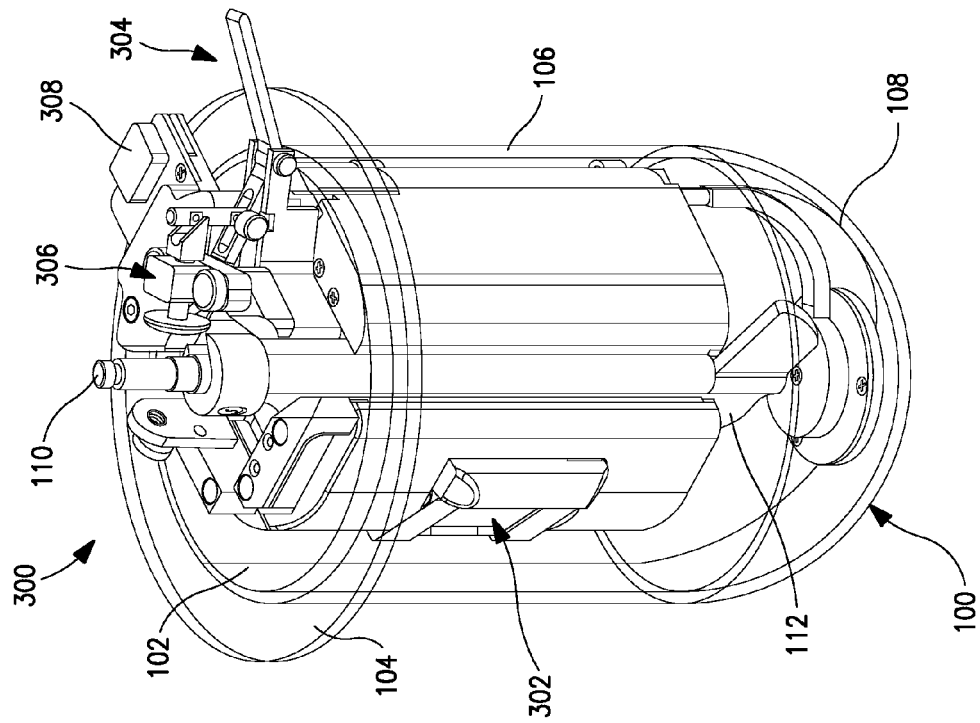
FIG. 3A and FIG. 3B are top perspective views of an example measurement device disposed within a vessel.
Figure 3B:
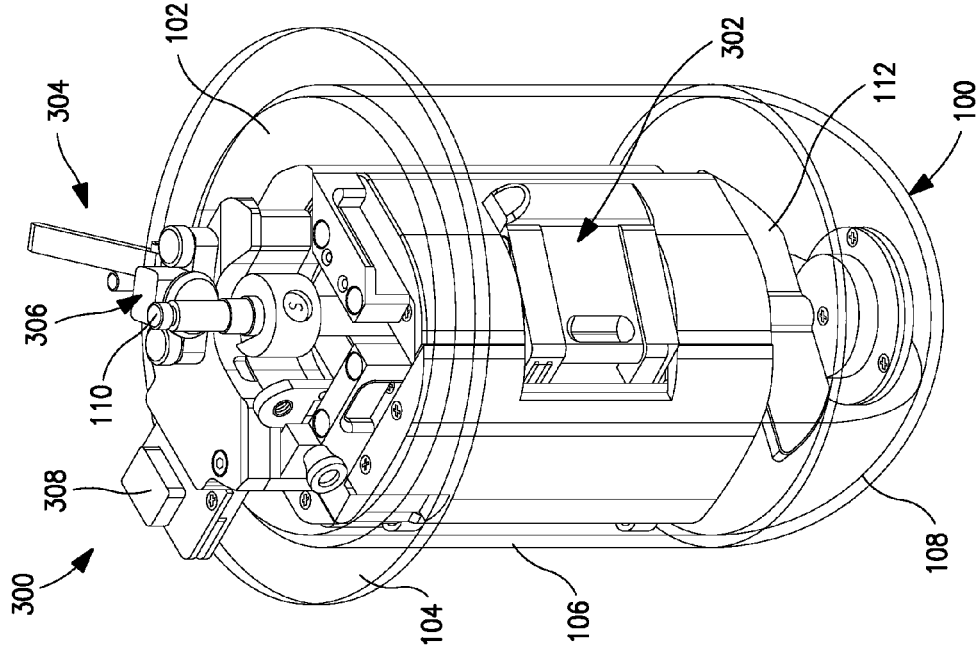

Referring now to FIG. 3A and FIG. 3B, an example measurement device 300 positioned within a vessel 100 in a typical testing position is shown. The example measurement device 300 includes both exterior components and interior components, the interior components being obscured by the exterior components of the measurement device 300. Additionally, the exterior components may include various subcomponents also obscured by the exterior components of the measurement device 300. The exterior components of the example measurement device 300 include: a centering system 302, a height gauge system 304, a basket wobble lifter 306, and a communication bus 308 for transmitting readings to and receiving communications from a data collection and control unit (not shown). The interior components not visible in FIGS. 3A-B but which will be described in further detail below in reference to subsequent figures include: a measurement unit, an inclinometer, and a rotational speed detector. As seen in FIGS. 3A-B, the measurement device 300 surrounds a shaft 110 disposed within a vessel 100. A paddle 112 at the end of the shaft 110 is positioned in the hemispherical lower end region 108 of the vessel 100.

Figure 4A:
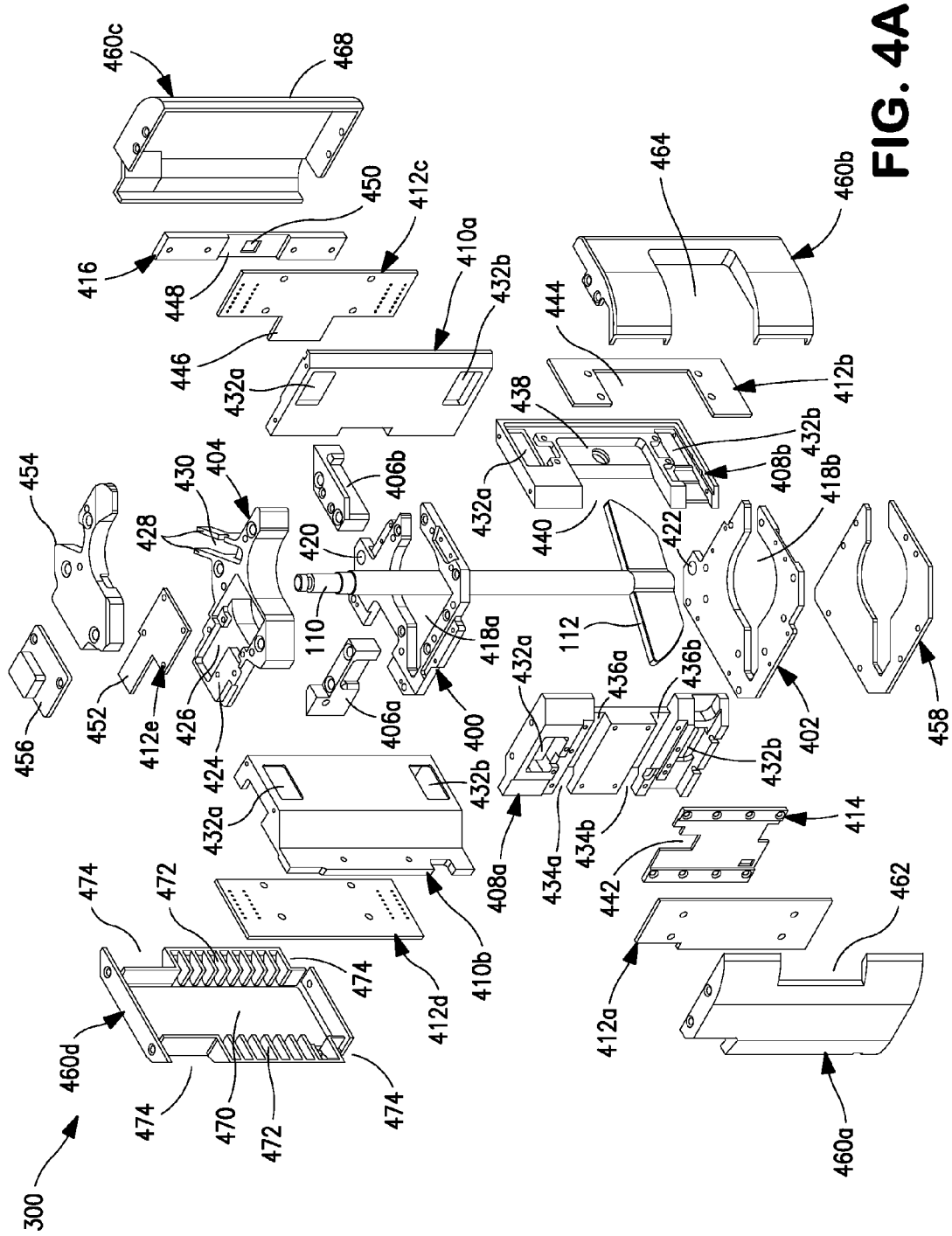
FIG. 4A and FIG. 4B are exploded top perspective views of structural and operational components of the example measurement device of FIGS. 3A and 3B.

Referring now to FIG. 4A, various structural components of an example measurement device 300 are shown in an exploded top perspective view. In particular, FIG. 4A illustrates various interior frame elements and exterior housing elements of an example measurement device in relation to a shaft 110 and paddle 112. The interior frame elements may provide the internal skeletal structure of the measurement device and/or may provide sites for securing various operational components (FIG. 4B) of the measurement device 300. The interior frame elements include: an upper retainer frame 400 and a lower retainer frame 402; an upper mounting frame 404; a first upper retainer wall 406a and a second upper retainer wall 406b; two light emitter frames 408a, 408b and two light receiver frames 410a, 410b; five printed circuit boards (PCB) 412a, 412b, 412c, 412d, 412e; and two PCB covers—a substantially square PCB cover 414 and a rectangular PCB cover 416.

As seen in the example measurement device 300 of FIG. 4A, the upper retainer frame 400 and the lower retainer frame 402 each include a central opening 418a, 418b through which the shaft 110 and shaft paddle 112 of a dissolution tester may pass. Additionally, the upper retainer frame 400 and the lower retainer frame 402 each include a respective bore 420, 422 formed at a corner of each frame.

The upper mounting frame 404 includes a tab 424 projecting in an outward direction. The tab 424 of the upper mounting frame 404 rests on the rim of a vessel, as seen in FIGS. 3A-B, when the measurement device 300 is installed in the vessel. The upper mounting frame 404 also includes a recess 426 formed in the upper surface 442 of the frame. The upper mounting frame 404 further includes two projections 428 extending outward and forming a channel 430 between the projections. In an assembled configuration, the upper mounting frame 404 is positioned above and mounted to the upper retainer frame 400 via screws or other suitable coupling means.

Likewise, a first upper retainer wall 406a and a second upper retainer wall 406b are mounted to a side edge of the upper retainer frame 400 on the surface of the frame. As seen in FIG. 4A, the first upper retainer wall 406a and the second upper retainer wall 406b are positioned and mounted to the surface of the upper retainer frame 400 such that the upper retainer walls 406a, 406b are substantially orthogonal relative to each other.

The light emitter frames 408a, 408b and the light receiver frames 410a, 410b each include an upper window 432a and a lower window 432b. The first light emitter frame 408a also includes an upper horizontal channel 434a and a lower horizontal channel 434b formed in the outer face of the first light emitter frame 408a. The first light emitter frame 408a also includes an upper slit 436a formed in the upper channel 434a and a lower slit 436b formed in the lower channel 434b. The second light emitter frame 408b includes an aperture 438 formed near the center of the frame. The second light emitter frame 408b also includes a vertical rectangular cutout 440 formed in the left side of the frame to the left of the aperture 438. The light emitter frames 408a, 408b and the light receiver frames 410a, 410b are positioned around and secured to the perimeter of the upper retainer and the perimeter of the lower retainer via one or more screws or other suitable coupling means. As shown in FIG. 4A, the light emitter frames 408a, 408b are positioned to be orthogonal relative to each other. Additionally, the first light receiver frame 410a is positioned opposite the first light emitter frame 408a, and the second light receiver frame 410b is positioned opposite the second light emitter frame 408b as seen in FIG. 4A. Accordingly, the light receiver frames 410a, 410b are also positioned orthogonally relative to one another.

Figure 4B:
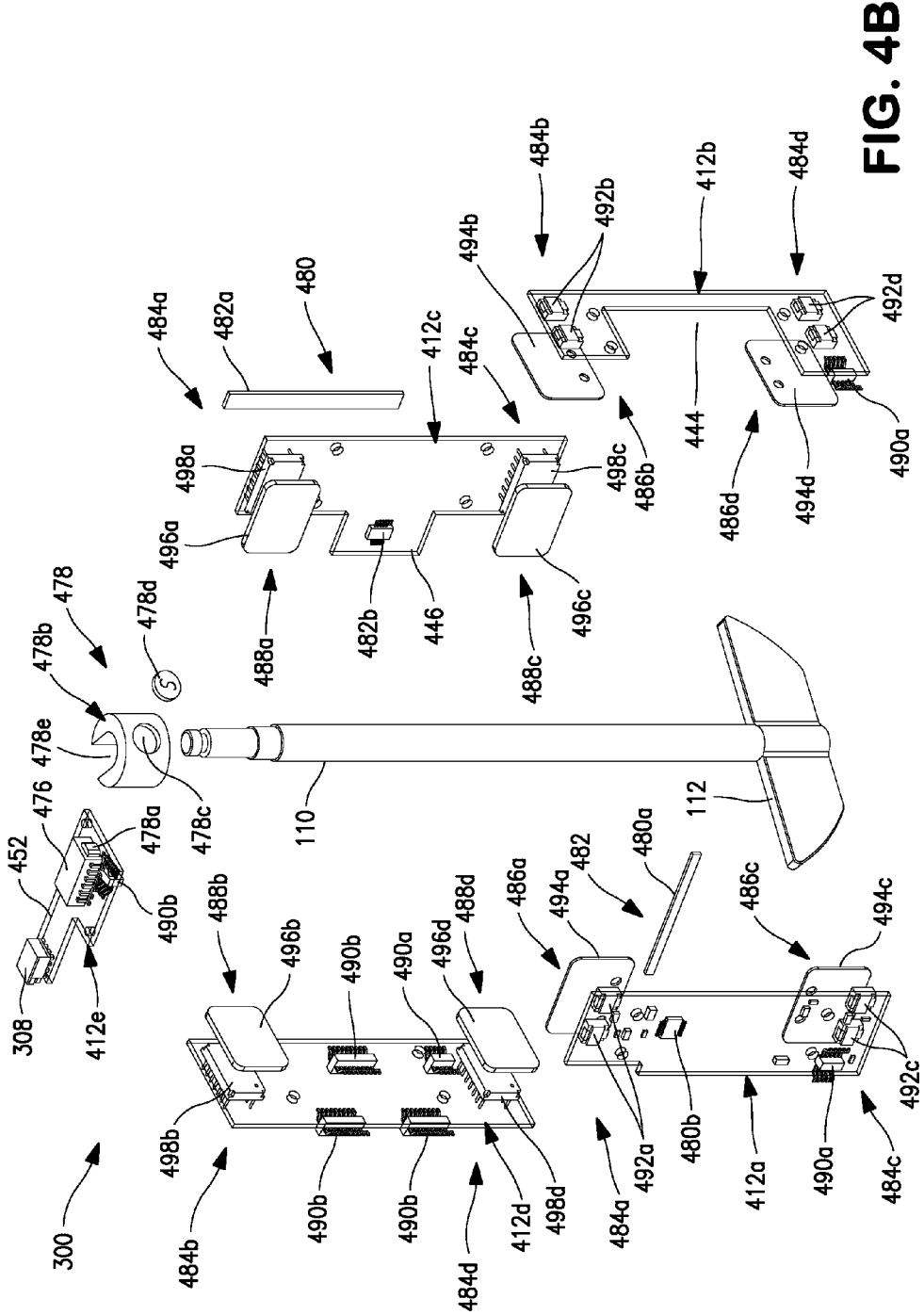

The PCBs serve as mounting locations for the electrical elements of the operational components (FIG. 4B). The first PCB 412a and square PCB cover 414 are attached to the exterior face of the first light emitter frame 408a with the square PCB cover 414 between the first PCB 412a and the frame. The square PCB cover 414 includes a cutout 442 formed near the center of the top of the cover. The second PCB 412b is attached to the exterior face of the second light emitter frame 408b. The second PCB 412b includes a cutout 444 on the left side of the PCB. The third PCB 412c includes a tab 446 extending outward on one side of the PCB. The rectangular PCB cover 416 includes a recess 448 formed near the center of the cover for receiving the tab 446 of the third PCB 412c. The recess 448 of the rectangular PCB cover 416 also includes a window 450 located near the center of the cover. The third PCB 412c and the rectangular PCB cover 416 are attached to the exterior side of the first light receiver frame 410a with the tab 446 of the third PCB 412c positioned between the first light receiver frame 410a and the recess 448 of the rectangular PCB cover 416. The fourth PCB 412d is attached to the exterior face of the second light receiver frame 410b. The fifth PCB 412e is attached to and positioned within the recess 426 of the upper mounting frame 404. The fifth PCB 412e also includes a tab 452 that extends into the tab 424 of the upper mounting frame as seen in FIG. 4A. The PCBs and PCB covers may be attached to the frames via one or more screws or other suitable coupling means.

Still referring to FIG. 4A, the exterior housing elements of the example measurement device 300 include: an upper mounting frame cover 454; a tab cover 456; a bottom cover 458; and four side wall housing panels 460a, 460b, 460c, 460d. The upper mounting frame cover 454 is attached to the upper surface of the upper mounting frame 404 via one or more screws or other suitable coupling means. The upper mounting frame cover 454 houses and protects the fifth PCB 412e positioned within the recess 426 of the upper mounting frame. Similarly, the tab cover 456 is attached to the upper surface of the tab 424 of the upper mounting frame 404 via one or more screws or other suitable coupling means. The tab cover 456 also houses and protects the tab portion 452 of the fifth PCB 412e positioned within the recess 426 of the upper mounting frame 404. Additionally, a bottom cover 458 is attached to the lower surface of the lower retainer frame 402 via one or more screws or other suitable coupling means.

The four side wall housing panels are positioned around and secured to the perimeter of the upper retainer frame 400 and the perimeter of the lower retainer frame 402. The side wall housing panels may be attached via one or more screws or other suitable coupling means. The first side wall housing panel 460a encloses the first PCB 412a attached to the first light emitter frame 408a. The first side wall housing panel 460a also includes a rectangular cutout 462 formed in the right side of the panel. The second side wall housing panel 460b encloses the second PCB 412b attached to the second light emitter frame 408b. The second side wall housing panel 460b also includes a substantially square cutout 464 formed in the left side of the panel. The third side wall housing panel 460c encloses the third PCB 412c attached to the first light receiver frame 410a. The third side wall housing panel 460c also includes a cavity 468 formed in the interior face of the panel. The fourth side wall housing panel 460d encloses the fourth PCB 412d attached to the second light receiver frame 410b. The fourth side wall housing panel 460d also includes a cavity 470 formed in the interior face of the panel. Additionally, baffles 472 line the right and left side of the interior cavity. Moreover, the fourth side wall housing panel 460b includes a cutout 474 formed at each of the four corners of the panel as shown in FIG. 4A.

In reference to FIG. 4B, an exploded top perspective view of the operational components of the example measurement device 300 is shown. The operational components of the measurement device 300, in this example, include: a communication bus 308 for exchanging communication signals between a data collection and control unit; an inclinometer 476; a rotational speed indicator 478; a centering arm measurement unit 480; a height gauge measurement unit 482; and multiple measurement units 484a, 484b, 484c, 484d. The measurement units 484a-d each include a light emitting component 486 and a light receiving component 488. In some implementations, the measurement units 484a-d may be, for example, optical micrometers.

As seen in the example measurement device 300 of FIG. 4B, some of the operational components are mounted to printed circuit boards. The PCBs of the example measurement device 300 of FIG. 4B also include various terminal strips for transmitting signals between the operational components mounted to the PCBs. For example, as shown in FIG.

4B, a terminal strip of a first type 490a is secured to each of PCBs 412a-d. Three terminal strips of a second type 490b are also secured to the fourth PCB 412d, and one terminal strip of the second type 490b is secured to the fifth PCB 412e as shown in FIG. 4B. Suitable terminal strips may be available from Samtec, Inc. as model designation FTSH-105-01-X-DH for the first terminal strip type 490a and model designation FTSH-110-01-X-DV for the second terminal strip type 490b.

A communication bus 308 is mounted to the exterior (upper) face of the fifth PCB 412e on the tab portion 452 of the fifth PCB 412e. The communication bus 308 is used to exchange communication signals between the operation components of the measurement device 300 and a data collection and control unit. The communication signals may include measurement signals from the operational components of the measurement device 300 and instructions for the operational components from the data collection and control unit. In the example measurement device 300 of FIG. 4B, the communication bus 308 may be a Mini USB 2.0 connector. A suitable USB unit may be available from Samtec, Inc. as model designation MUSB-05-S-B-SM-A. The operation of the communication bus 308 will be described in further detail below.

The example measurement device 300 of FIG. 4B also includes an inclinometer 476. Those skilled in the art understand that an inclinometer, also referred to as a tilt meter or level meter, measures angles of inclination with respect to gravity. In the example measurement device 300 of FIG. 4B, the inclinometer 476 is mounted to the fifth PCB 412e and can measure inclination along two axes. In the example shown, the inclinometer 476 senses the angular position of the vessel relative to the vertical axis of the vessel and generates signals corresponding to the angular position of the vessel. A suitable dual axis inclinometer may be available from VTI Technologies as model designation SCA100T. The operation of the inclinometer 476 will be described in further detail below.

The example measurement device 300 of FIG. 4B additionally includes a rotational speed indicator 478 for determining the rotational speed of the shaft 110 during operation. The rotational speed indicator includes sensor 478a and a mounting component 478b having a recess 478c that holds a disc-shaped magnet 478d. In the example shown, the mounting component 478b is a magnet ring, and the disc-shaped magnet 478d has a north pole on one face and a south pole on an opposite face. As shown in FIG. 4B, the south pole of the magnet faces outward away from the magnet ring 478b, and the north pole of the magnet 478d faces inward towards the magnet ring 478b. The magnet ring 478b includes a notch 478e for mounting the magnet ring 478b to the shaft 110. Accordingly, the magnet ring 478b will rotate simultaneously with the shaft 110 during operation. The sensor 478a may be, for example, a Hall-effect sensor that senses the rotation of the shaft 110 as the magnet 478d passes by the sensor during each rotation. The sensor 478a generates a signal corresponding for each sensed rotation of the shaft 110, and the measurement device 300 tracks the number of rotations. The measurement device 300 or an external calculation unit may calculate rotational speed RPM as the number of rotations during a predetermined time period, such as, for example, the number of rotations in a five (5) second time period.

The example measurement device 300 of FIG. 4B further includes the operational sub-components of a centering arm measurement unit 480 and a height gauge measurement unit 482. In particular, the centering arm measurement unit 480 and includes a horizontal magnetic strip 480a used to determine the position of the centering arm (FIGS. 7A-E). Likewise, the height gauge measurement unit 482 includes a vertical magnetic strip 482a used to determine the position of the height gauge arm.

The magnetic strips 480a, 482a of the centering arm measurement unit 480 and the height gauge measurement unit 482 are respectively positioned adjacent to a transducer 480b, 482b. The transducer 480b, in the example shown, is mounted to the interior face of the first PCB 412a and interfaces with the horizontal magnetic strip 480a of the centering arm measurement unit 480. The transducer 482b is, in the example shown, mounted to the exterior face of the third PCB 412c and interfaces with the vertical magnetic strip 482a of the height gauge measurement unit 482.

In the example measurement device 300 of FIG. 4B, each transducer 480b, 482b is a magnetic linear displacement sensor that uses Hall-effect principles to sense the displacement of the centering arm measurement unit 480 and the height gauge measurement unit 482. The magnetic strips 480a and 482a may be, for example, multi-pole magnetic strips that include a sequence of individual magnets of reversing polarities (i.e., N-S-N-S-...). The multi-pole magnetic strips 480a, 482a move across the face of the magnetic linear displacement sensors 480b and 482b respectively, which sense the reversing polarities of the individual magnets as the magnetic strips move back and forth. In turn, the magnetic linear displacement sensors 480b, 482b generate signals corresponding to the movement and position of the magnetic strips 480a, 482a. A suitable magnetic linear displacement sensor may be available from Austria Microsystems AG as model designation AS5306 Linear Encoder IC. As explained further below, the signals from the magnetic linear displacement sensors 480b, 482b are used, for example, when calculating the center of the vessel 100 and/or the height of the paddle/basket 112 at the end of the shaft 110.

The example measurement device 300 of FIG. 4B also includes multiple measurement units 484a, 484b, 484c, 484d. In the example shown, the measurement units 484a-d are optical micrometers respectively including a light emitting component 486a, 486b, 486c, 486d and a light receiving component 488a, 488b, 488c, 488d. Generally, a light emitting component and a light receiving component of an optical micrometer are positioned apart from and facing each other as shown by way of example in FIG. 4B. The light emitting components 486a-d illuminate a target positionable between the light emitting components and the light receiving components 488a-d of the optical micrometers 484a-d. The light emitting components 486a-d emit light towards the corresponding light receiving components 488a-d. Further, the light receiving components 488a-d may generate signals corresponding to the light received from the corresponding light emitting components 486a-d. The signals generated by a light receiving component 488a-d may be transmitted to a calculation unit for further processing.

By way of example and as seen in FIG. 4B, a shaft 110 serves as a target positioned between the light emitting components 486a-d and the respective light receiving components 488a-d of the optical micrometers 484a-d. Accordingly, the target (shaft 110) casts a shadow on the light receiving components 488a-d of the optical micrometers 484a-d when illuminated by the light emitting components 486a-d. Based on the shadow cast by the target (shaft 110) and the resulting signals generated by the light receiving components 488a-d, a calculation unit can calculate and determine various parameters relating to the target, such as the size and the position of the target.

In the example measurement device of FIG. 4B, the light emitting components 486a-d of the optical micrometers 484a-d are mounted to the first PCB 412a and the second PCB 412b. The light emitting components 486a-d of the optical micrometers 484a-d include a pair of adjacent LED units 492a, 492b, 492c, 492d and light emitter filters 494a, 494b, 494c, 494d positioned in front of the LED units 492a-d. The LED units 492a-d may be, for example, high-powered reflective mirror-type LEDs that may reflect visible or infrared light. Those skilled in the art will understand that a high-powered reflective mirror-type LED reflects light from a mirror inside the unit such that the light is radiated outward as a parallel beam. A suitable LED unit may be available from Alpha-One Electronics Ltd. as model designation AOP1-8505.

Further, light emitter filters 494a-d may be positioned adjacent to the LED units 492a-d in order to filter the light from the LED units 492a-d. The light emitter filters 494a-d may be designed to filter a particular wavelength or wavelength range such as, for example, the particular wavelength of light emitted by the LED units 492a-d. In some example embodiments, a collimating lens rather than a filter may be placed adjacent to the LED units 492a-d. Those skilled in the art will understand that a collimating lens may be used to align rays of light in a specific direction or to narrow a beam of light by reducing the size of the cross-section of the beam.

The light receiving components 488a-d of the example measurement device 300 of FIG. 4B are correspondingly mounted to the third PCB 412c and fourth PCB 412d. The light receiving components 488a-d of the optical micrometers 484a-d also include a light receiver filter 496a, 496b, 496c, 496d positioned in front of a liner sensor array 498a, 498b, 498c, 498d respectively. The linear sensor arrays 498a-d receive the light emitted from the corresponding LED units 492a-d filtered through the corresponding filters 496a-d. Like the light emitter filters 494a-d, the light receiver filters 496a-d may also be used to filter the light received from the LED units 492a-d before the light reaches the linear sensor array. Further, the filter may be designed to filter the type of light the linear sensor array is designed to detect.

The linear sensor arrays 498a-d may include a sequence of photodiodes (pixels) aligned to form a pixel array. The pixel array of a linear sensor array may be, for example, a contiguous 256×1 pixel array. Each pixel may generate a current signal when the pixel receives light energy. As explained further below, the signals from the linear sensor arrays 498a-d may be used when calculating the location and position of the shaft 110 within a vessel 100. A suitable linear sensor array may be available from Texas Advanced Optoelectronic Solutions® as model designation TSL1402R.

As seen in FIG. 4B, the example measurement device 300 includes an upper pair of optical micrometers 484a, 484b and a lower pair of optical micrometers 484c, 484d. Each optical micrometer pair includes co-planar and orthogonally positioned light emitting components 486a-486b, 486c-486d and corresponding co-planar and orthogonally positioned light receiving components 488a-488b, 488c-488d.

The LEDs 492a of the light emitting component 486a and filter 494a of the first upper micrometer 484a are mounted on the interior face and near the top of the first PCB 412a. The LEDs 492b of the light emitting component 486b and filter 494b of the second upper micrometer 484b are mounted on the interior face and near the top of the second PCB 412b. Because the first PCB 412a and the second PCB 412b are orthogonal relative to each other, the LEDs 492a and filter 494a of the first upper micrometer 484a are also orthogonal relative to the LEDs 492b and filter 494b of the second upper micrometer 484b as seen in FIG. 4B.

Similarly, the linear sensor array 498a and filter 496a of the first upper micrometer 484a are mounted on the interior face of the third PCB 412c. The linear sensor array 498b and filter 496b of the second optical micrometer 484b are mounted to the interior face of the fourth PCB 412d. In this configuration, the linear sensor arrays 498a-b and filters 496a-b are respectively positioned opposite of and facing the corresponding LEDs 492a-b and filters 494a-b of the first upper micrometer pair 484a-b. Because the third PCB 412c and the fourth PCB 412d are orthogonal relative to each other, the linear sensor array 498a and filter 496a of the first upper micrometer 484a are also orthogonal relative to the linear sensor array 498b and filter 496b of the second optical micrometer 484b. The example measurement device 300 of FIG. 4B also includes a lower pair of optical micrometers 484c, 484d. The first optical micrometer 484c and second optical micrometer 484d of the lower pair are positioned in an orthogonal configuration similar to the configuration of the upper pair of optical micrometers 484a-b as described above and as seen in FIG. 4B.

The measurement units 484a-d may be calibrated prior to calculating the position and location of a shaft within a vessel during a testing routine. During calibration, a calibration shaft may be accurately placed in the center of the vessel such that the calibration shaft is centered in the vessel. The output signals from each linear sensor array 498a-d may then be measured and recorded as reference values for the centered shaft. The stored reference values for a centered shaft may then be used when calculating the location and position of a shaft being tested as explained further below.

In an alternative embodiment, the measurement device 300 may utilize a single point light source centered with a linear sensor array rather than a pair of adjacent LEDs units as in the example embodiment described above. In the example alternative embodiment, the light emitting component may utilize a single point light source such as, for example, a single LED to illuminate the shaft. A suitable single point light source may be available from Marubeni Corp. as model designation SMT770. Additionally, a suitable linear sensor array that may be used with example embodiments having a single point light source may also be available from Hamamatsu Photonics, K.K. as model designation S11108. Example embodiments that use a single point light source may use an alternative set of equations when calculating the center position of the shaft. The alternative set of equations is discussed further below with reference to FIG. 16.

Figure 5:
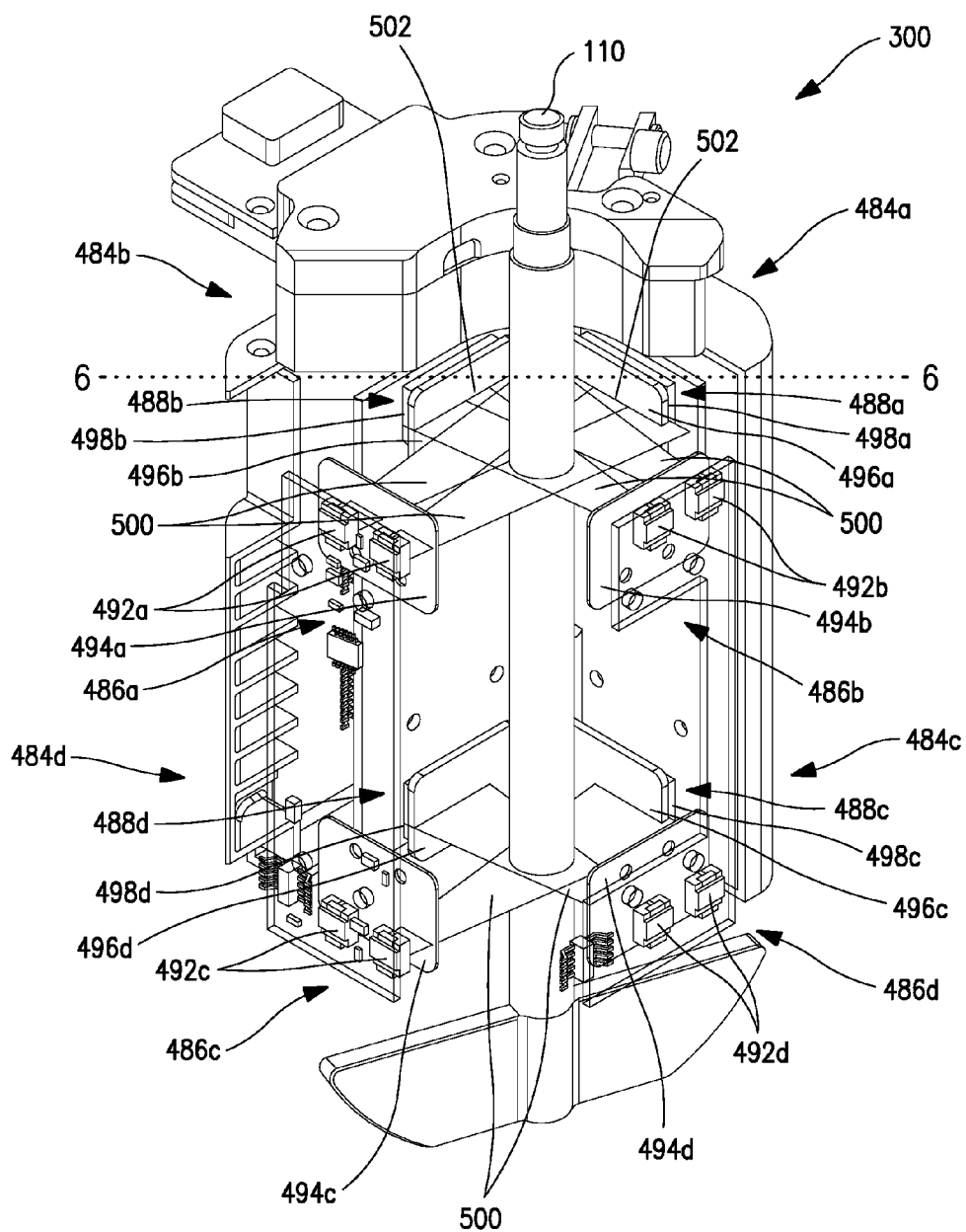
FIG. 5 is a cut-away perspective view of the example measurement device of FIGS. 3A and 3B.

Referring now to FIG. 5, a cutaway view of an assembled example measurement device 300 is shown. In particular, the light emitting components 486a-d and light receiving components 488a-d of the upper pair of optical micrometers 484a-b and the lower pair of optical micrometers 484c-d are shown. As shown, light 500 from the LEDs of the light emitting components 486a-d is directed towards the light receiving components 488a-d. As can be seen in FIG. 5, some of the light strikes the shaft 110 instead of the light receiving components 488a-d. Other light 500 travels past the shaft 110 to strike the light receiving components 488a-d. Accordingly, the shaft 110 casts a shadow 502 on the light receiving components 488a-d of the optical micrometers 484a-d. In an assembled configuration, the upper windows 432a and the lower windows 432b (FIG. 4A) provide a frame around the perimeter of the light emitting components 486a-d and light receiving components 488a-d. Accordingly, in an assembled configuration, the filters 494a-d are positioned between the LEDs 492a-d and the frame windows 432a-b, and the filters 496a-d are positioned between the linear sensor arrays 498a-d and the frame windows 432a-b.

FIG. 5 also illustrates that the orthogonal configuration enables the light 500 from the light emitting components 486a-d of the optical micrometers 484a-d to intersect when illuminating the shaft 110 as seen in FIG. 5. Those skilled in the art will recognize that the light emitting components of the optical micrometers may be positioned at non-orthogonal angles relative to one another. Accordingly, other configurations may also result in the intersection of light from the light emitting components of the optical micrometers.

Figure 6:
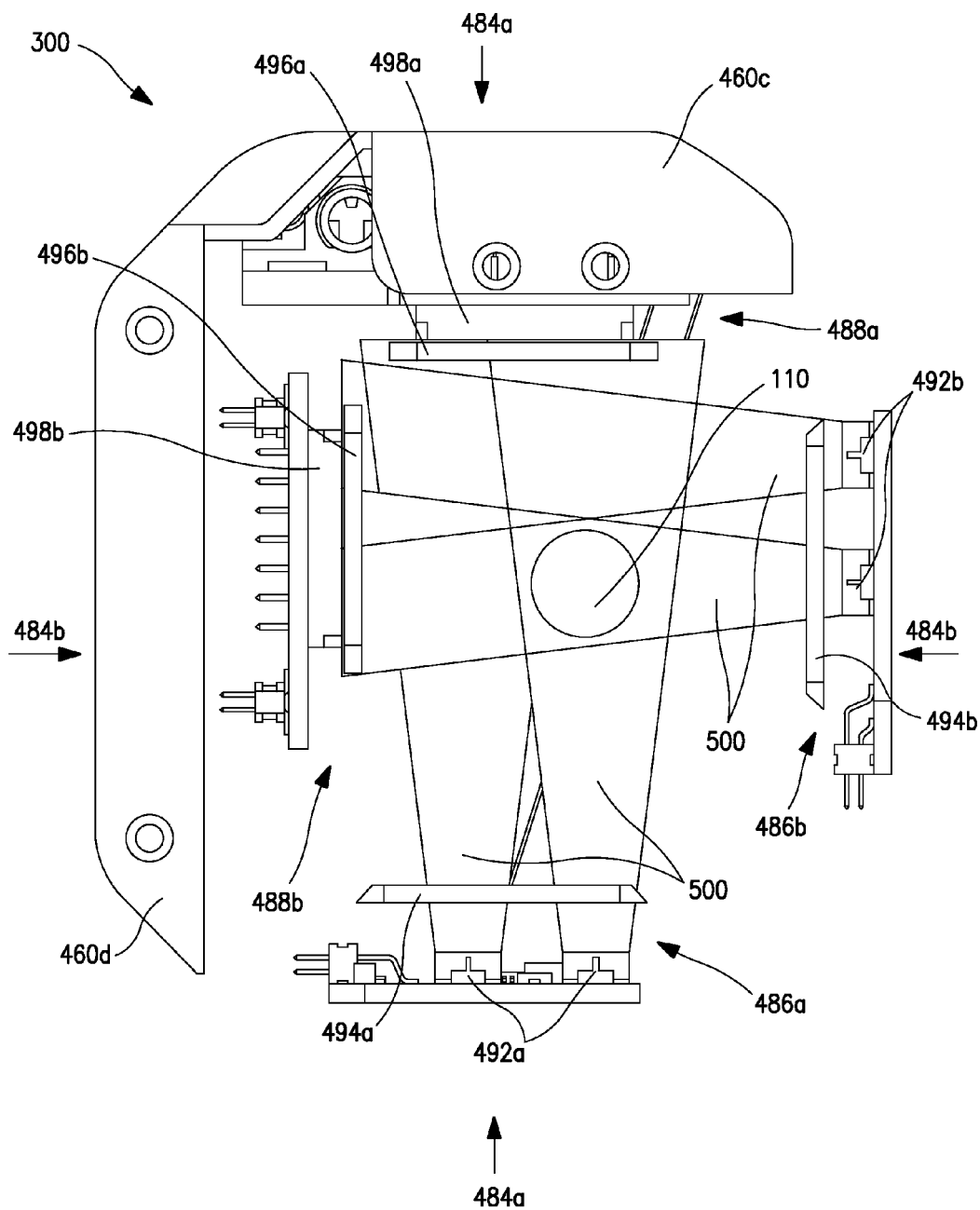
FIG. 6 is a top cross-sectional view of the example measurement device of FIG. 5 along line 6-6.

The intersection of light 500 from the light emitting components 486a-b of the optical micrometers 484a-b is also shown in FIG. 6. As seen in FIG. 6, the LEDs 492a of the first upper optical micrometer 484a emit light 500 towards the light receiving component 488a of the first upper optical micrometer 484a. The light 500 from the LEDs 492a passes through the filters 494a, and illuminates the shaft 110. The light 500 that does not strike the shaft 110 continues toward the light receiving component 488a where the light passes through the filter 496a before striking the linear sensor array 498a. Accordingly, the shaft 110 prevents some of the light 500 from reaching the light receiving component 488a and casts a shadow 502 on the linear sensor array 498a. The linear sensor array 498a generates signals corresponding to the light 500 received from the LEDs 492a or not received due to the obstruction of the shaft 110.

Likewise and as seen in FIG. 6, the LEDs 492b from the second upper optical micrometer 484b emit light 500 in an orthogonal direction relative to the light from the first upper optical micrometer 484a. As shown, the light 500 from the second upper optical micrometer 484b intersects the light from the first upper optical micrometer 484a. A similar interaction of light occurs with respect to the lower pair of optical micrometers 484c-d. Based on the signals received from the linear sensor arrays 498a-d, a calculation unit can determine various parameters relating to the shaft 110 including the dimension of the shaft, the center offset of the shaft, the angular offset of the shaft, shaft wobble, and basket wobble. The determination of various shaft and vessel parameters based on the signals from the optical micrometers will be discussed below in more detail.

Figure 7A:
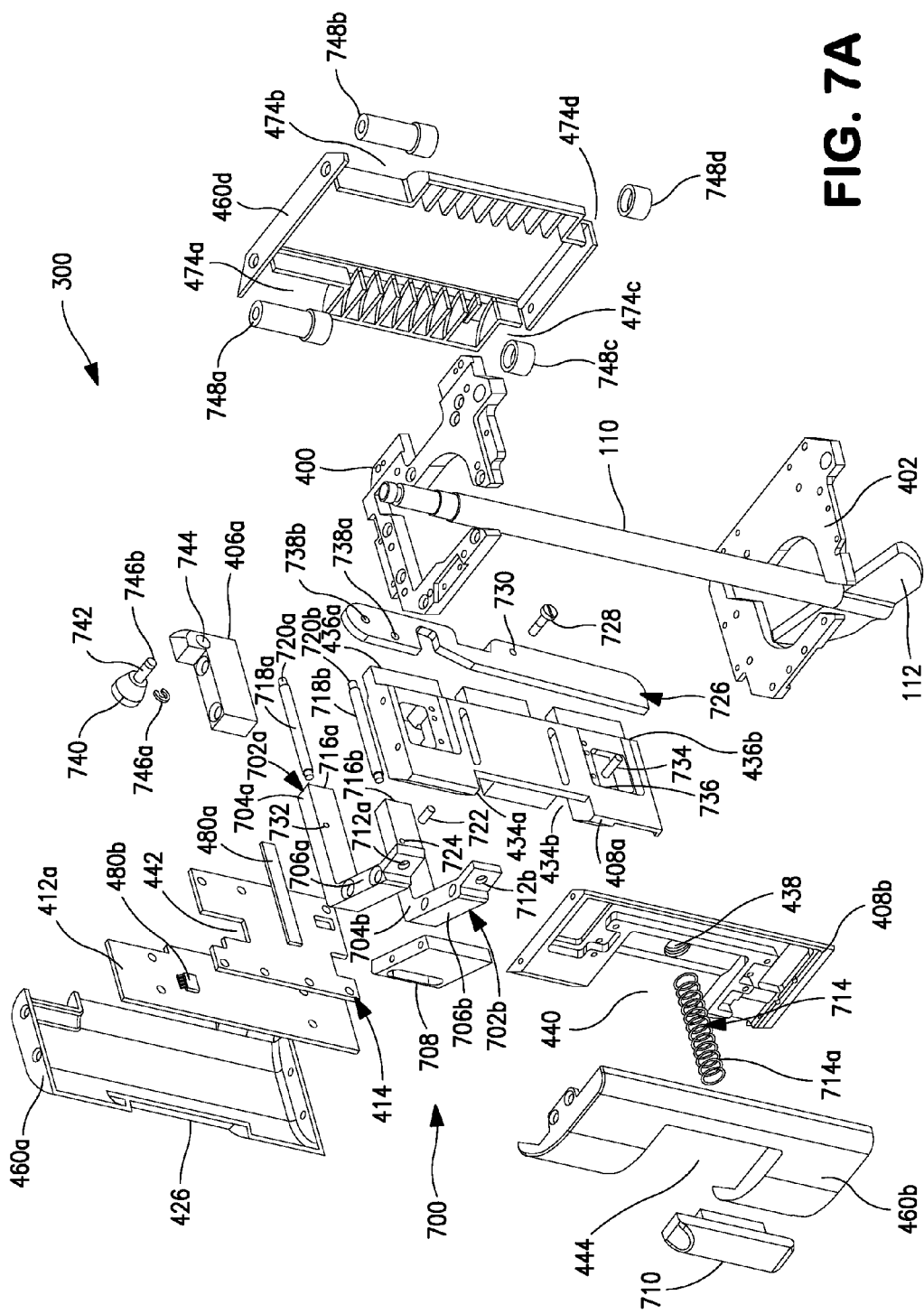
FIG. 7A is an exploded perspective view of a device centering system for the example measurement device of FIGS. 3A and 3B.

Referring now to FIG. 7A, an exploded perspective view of a device centering system 302 of an example measurement device 300 shows the components relating to the centering arm 700 of the measurement device in relation to a shaft 110. The centering arm 700 is a laterally displaceable arm used to secure the measurement device 300 to the interior side wall 106 of the vessel 100. As seen in FIG. 7A, the cutout 462 of the first side wall housing panel, the cutout 440 of the second light emitter frame, the cutout 464 of the second side wall housing panel, and the cutout 444 of the second PCB provide a space for the centering arm 700 to move inward and outward when the measurement device 300 is in an assembled configuration. The centering arm 700 includes an upper strut 702a and a lower strut 702b positioned substantially parallel relative to each other. Each strut 702a-b includes a respective longitudinal portion 704a, 704b and angled portion 706a, 706b. As discussed above in reference to FIG. 4A, the first light emitter frame 436a includes an upper channel 434a and a lower channel 434b formed on the exterior face of the frame. The upper strut 702a and the lower strut 702b of the centering arm 700 may respectively be received within these channels 436a, 436b, and the channels 436a, 436b provide for lateral movement of the struts 702a, 702b. A connector panel 708 connects the upper strut 702a to the lower strut 702b. The connector panel 708 is attached to the respective angled portions 706a-b of the struts 702a-b via one or more screws or other suitable coupling means. Further, the connector panel 708 may be made of rigid plastic or other suitable material.

A contact point 710 is also positioned between the upper strut 702a and lower strut 702b. The contact point 710 may be attached at the respective terminal ends 712a, 712b of the angled portions 706a-b of the struts 702a-b adjacent to the connector panel 708. The contact point 710 may be, for example, a rigid plastic bumper as shown in the example measurement device 300 of FIG. 7A. The contact point 710 may also include a recess (not shown) for receipt of one end of a spring 714. An end 714a of the spring 714 may be disposed within the recess of the contact point 710. The other end of the spring 714 may be mounted in the aperture 438 of the second light emitter frame 408b. In this example configuration, the spring 714 compresses against the second light emitter frame 408b of the measurement device 300 and applies an outwardly biasing force on the centering arm 700, which naturally disposes the centering arm in an outward displacement relative to the measurement device.

The struts 702a-b may also each include a duct 716a, 716b respectively formed along the length of and within the longitudinal portions 704a-b of the struts 702a-b. A centering spring 718a, 718b may be respectively disposed within each duct 716a-b such that a portion 720a-b of each centering spring 718a, 718b extends out of the ducts and away from the struts 702a-b. The centering springs 718a-b permit lateral movement of the struts 702a-b along the length of the centering springs 718a-b and through the channels 434a-b of the first light emitter frame 408a. The lower strut 702b includes a mechanical stop 722 to restrict the range of movement of the centering arm 700.

In the example measurement device 300 of FIG. 7A, the mechanical stop 722 is a dowel disposed within a bore 724 formed in the interior face of the lower strut 702b and extending into the lower slit 436b formed through the first light emitter frame 408a. Accordingly, the inward range of movement of the centering arm 700 is restricted by the dowel 722 and the lower slit 436b formed in the flame 408a. As the centering arm 700 moves inward, the dowel 722 will eventually contact the end of the lower slit 436b preventing further inward movement of the centering arm 700.

The example measurement device 300 of FIG. 7A also includes a retaining lever 726 to secure the centering arm 700 in an inwardly displaced position. The retaining lever 726 of the example measurement device 300 is a flat elongate rod positioned adjacent to the interior face of the first light emitter frame 408a. The retaining lever 726 is attached to the upper strut 702a via a screw 728 or other suitable coupling means. In the example measurement device 300 of FIG. 7A, the screw 728 is inserted through a bore 730 formed in the retaining lever 726, passes through the upper slit 436a formed in the first light emitter frame 408a, and is received by a bore 732 formed in the interior face of the upper strut 702a. Accordingly, the retaining lever 726 moves laterally in conjunction with the centering arm 700. For example, as the centering arm 700 moves inward and outward, the retaining lever 726 moves inward and outward as well.

Figure 7C:
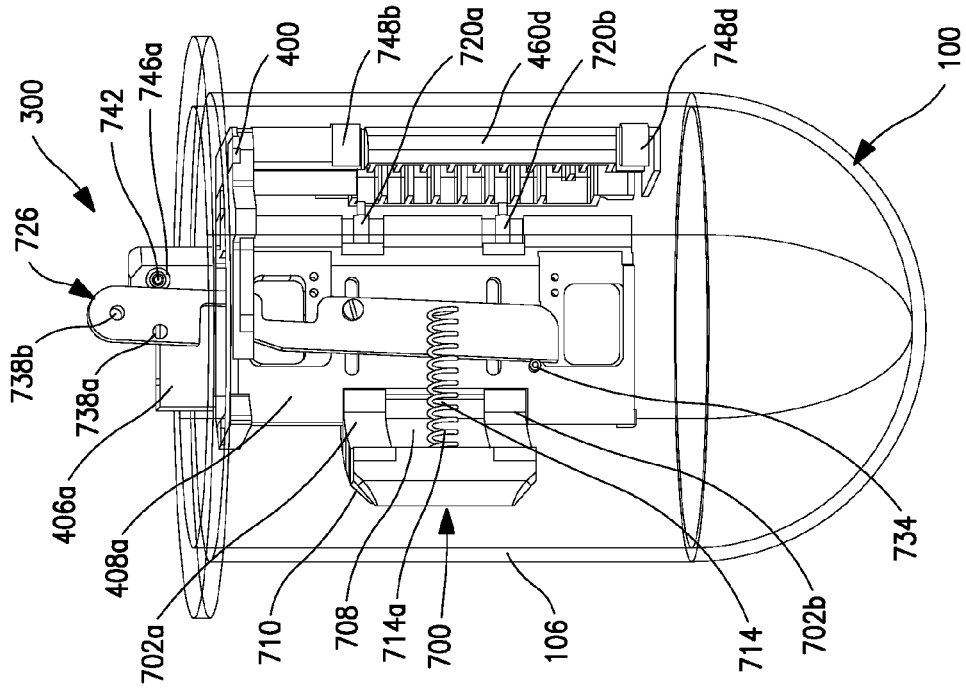
FIG. 7B and FIG. 7C are side views of an assembled device centering system of the example measurement device of FIG. 7A disposed within a vessel.

Further, the outward movement of the retaining lever 726 and thus the centering arm 700 is also restricted by a mechanical stop 734. In the example measurement device 300 of FIG. 7A, the mechanical stop 734 for the retaining lever 726 is also a dowel. The dowel 734 is disposed within a bore 736 formed in the interior face of the first light emitter frame 408a. As can be seen in FIG. 7C, as the centering arm 700 and retaining lever 726 move in an outward direction the retaining lever 726 will eventually contact the dowel 734 preventing further outward movement of the centering arm 700.

Moreover, in the example retaining lever 726 of FIG. 7A, the retaining lever 726 includes a first retaining hole 738a and second retaining hole 738b near the top of the retaining lever 726. The first retaining hole 738a may mesh with a securing component 740 to secure the centering arm 700 in an inwardly displaced position while the spring is compressed. In the example shown, the securing component 740 is a retaining knob attached to the first upper retainer wall 406a. The retaining knob 740 includes a pin 742 that passes through a bore 744 formed in through the first upper retainer wall 406a. As seen in the top view of FIG. 7D, the pin 742 protrudes through the bore 744 towards the interior of the measurement device 300 and is positioned next to the retaining lever 726. The retaining knob 740 is secured to the first upper retainer wall 406a via an e-style retaining ring 746a attached to a groove 746b formed around the circumference of the knob pin 742.

The upper strut 702a of the centering arm 700 also includes a magnetic strip 480a attached to the external face of the upper strut 702a used to determine the position of the centering arm 700 when installed in a vessel. As discussed above with reference to FIG. 4B, the magnetic strip 480a interfaces with a liner encoder 480b mounted to the interior face of the first PCB 412a to sense a linear displacement of the centering arm 700 and generates signals corresponding to the position of the centering arm 700. A square PCB cover 414 is positioned between the first PCB 412a and the upper strut 702a and lower strut 702b of the centering arm 700. The PCB cover 414 covers a portion of the first PCB 412a but includes a cutout 442 to expose the linear encoder 480b to the magnetic strip 480a on the upper strut 702a of the centering arm 700. Thus, the linear encoder 480b may sense the position of the magnetic strip 480a when the centering arm 700 is positioned within a vessel 100 and secured to the lateral side 106 of the vessel.

Still referring to FIG. 7A, the measurement device 300 are fixed contact points 748a, 748b, 748c, 748d that may be attached to the fourth side wall housing panel 460d. The contact points 748a-d may be attached to the fourth side wall housing panel 460d via a screw or other suitable coupling means. As shown in FIG. 7A, the fixed contact points 748a-d are respectively positioned in each cutout 474 at the four corners of the fourth side wall housing panel 460d. In the example measurement device 300 seen in FIG. 7A, the fixed contact points 748a-d are cylindrical rigid plastic bumpers. Like the contact point 710 of the centering arm 700, the fixed contact points 748a-d press against the lateral side wall 106 of the vessel when the measurement device is installed in a vessel. Accordingly, the contact point 710 of the centering arm 700 and the fixed contact points 748a-d are used to accurately locate the measurement device 300 within the vessel as explained further below.

Figure 7B:
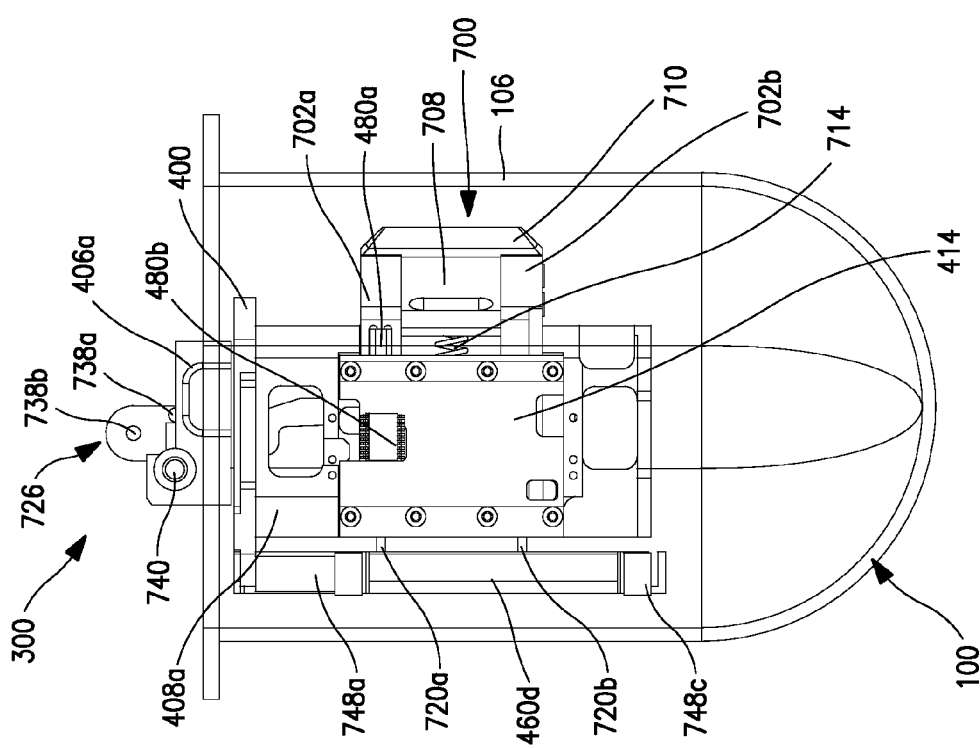
Figure 7E:
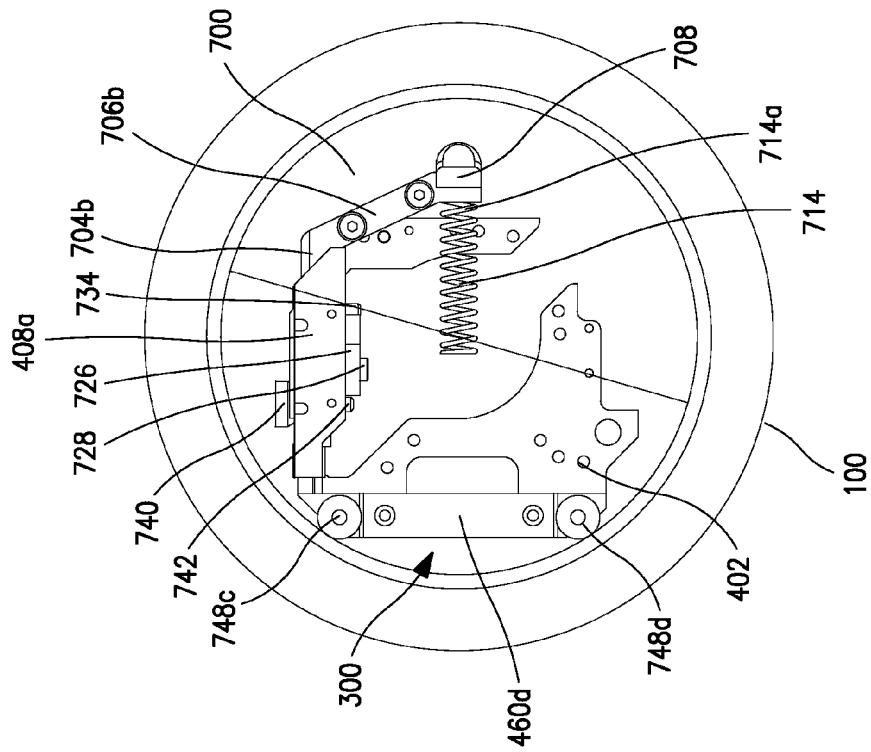
FIG. 7E is a bottom view of an assembled centering system of the example measurement device of FIG. 7A disposed within a vessel.
Figure 7D:
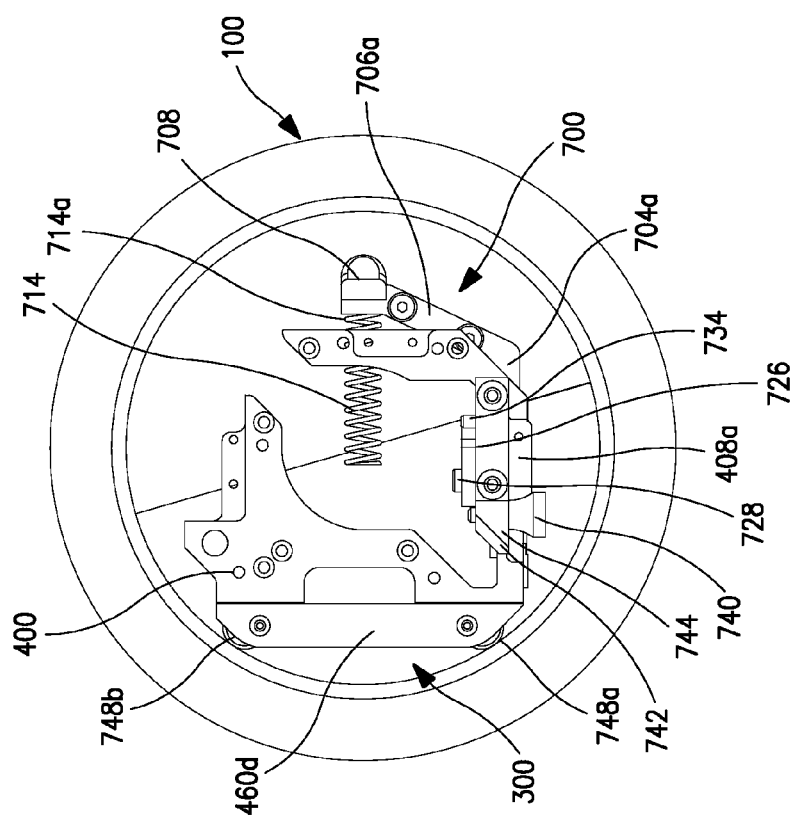
FIG. 7D is a top view of an assembled centering system of the example measurement device of FIG. 7A disposed within a vessel.

The operation of the centering arm 700 will now be discussed with reference to FIGS. 7C-E. As an operator pushes the centering arm 700 inward towards the measurement device 300, the spring 714 resists the inward movement as can be seen from FIG. 7C. If the operator were to release the centering arm 700, the outwardly biased force applied to the centering arm 700 by the spring 714 would return the centering arm 700 to an outwardly displaced position as shown in FIGS. 7B-C. However, an operator may push the centering arm 700 inward until the first retaining hole 738a of the retaining lever 726 aligned with the pin 742 of the retaining knob 740 as can been seen from FIG. 7D. Once appropriately aligned, the pin 742 of the retaining knob 740, would mesh with the first retaining hole 738a of the retaining lever 726 and secure the centering arm 700 in an inwardly displaced position relative to the measurement device 300.

Similarly, an operator may return the centering arm 700 to an outwardly displaced position relative to the measurement device 300 by uncoupling the retaining lever 726 from the retaining knob 740. Once the retaining lever 726 is uncoupled from the retaining knob 740, the spring 714 applies an outwardly biasing force to push the centering arm 700 away from the measurement device 300. As discussed above, the outward movement of the centering arm 700 is restricted by the interaction of the retaining lever 726 with the mechanical stop 734.

Accordingly, an operator would properly place the measurement device 300 within a vessel 100 by taking the following steps. First an operator would depress the centering arm 700 until the retaining lever 726 coupled to the retaining knob 740. Then, the operator would insert the measurement device 300 into a vessel 100 as seen in FIGS. 7B-E. As shown in FIGS. 7D-E, while the centering arm 700 is in an inwardly depressed position, a gap exists between the contact point 710 of the centering arm and the lateral side wall 106 of the vessel. An operator may then uncouple the retaining lever 726 from the retaining knob 740, and the spring 714 will apply an outwardly biasing force on the centering arm 700. As the centering arm 700 moves outward, it will eventually come into contact with the lateral side wall 106 of the vessel 100 and secure the measurement device 300 within the vessel 100. In a secured configuration, the linear encoder 480b interfaces with the magnetic strip 480a, and the linear encoder 480b generates a signal corresponding to the position of the centering arm 700.

Figure 8A:
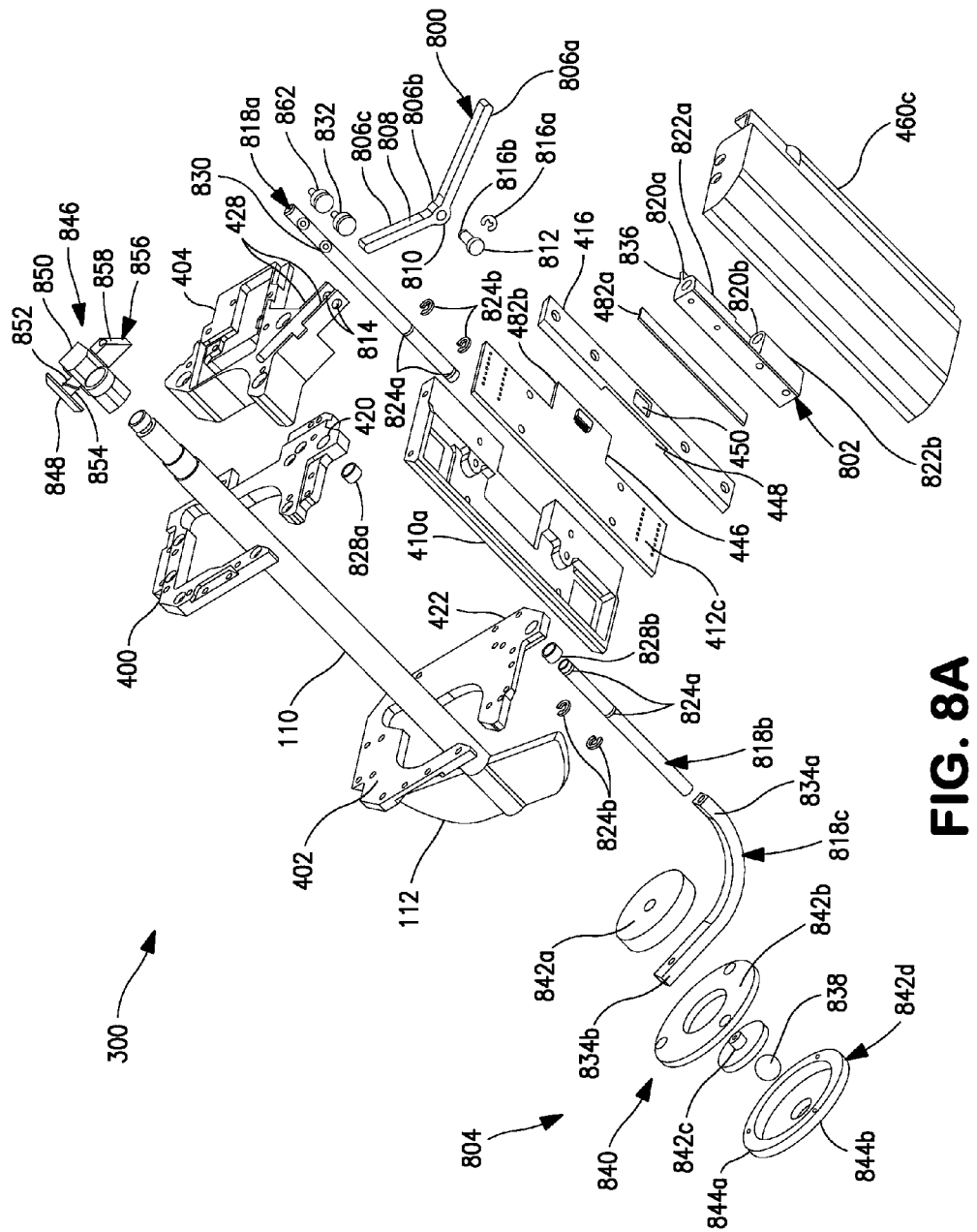
FIG. 8A is an exploded perspective view of a height measurement system and a basket wobble lifter of an example measurement device.
Figure 8B:
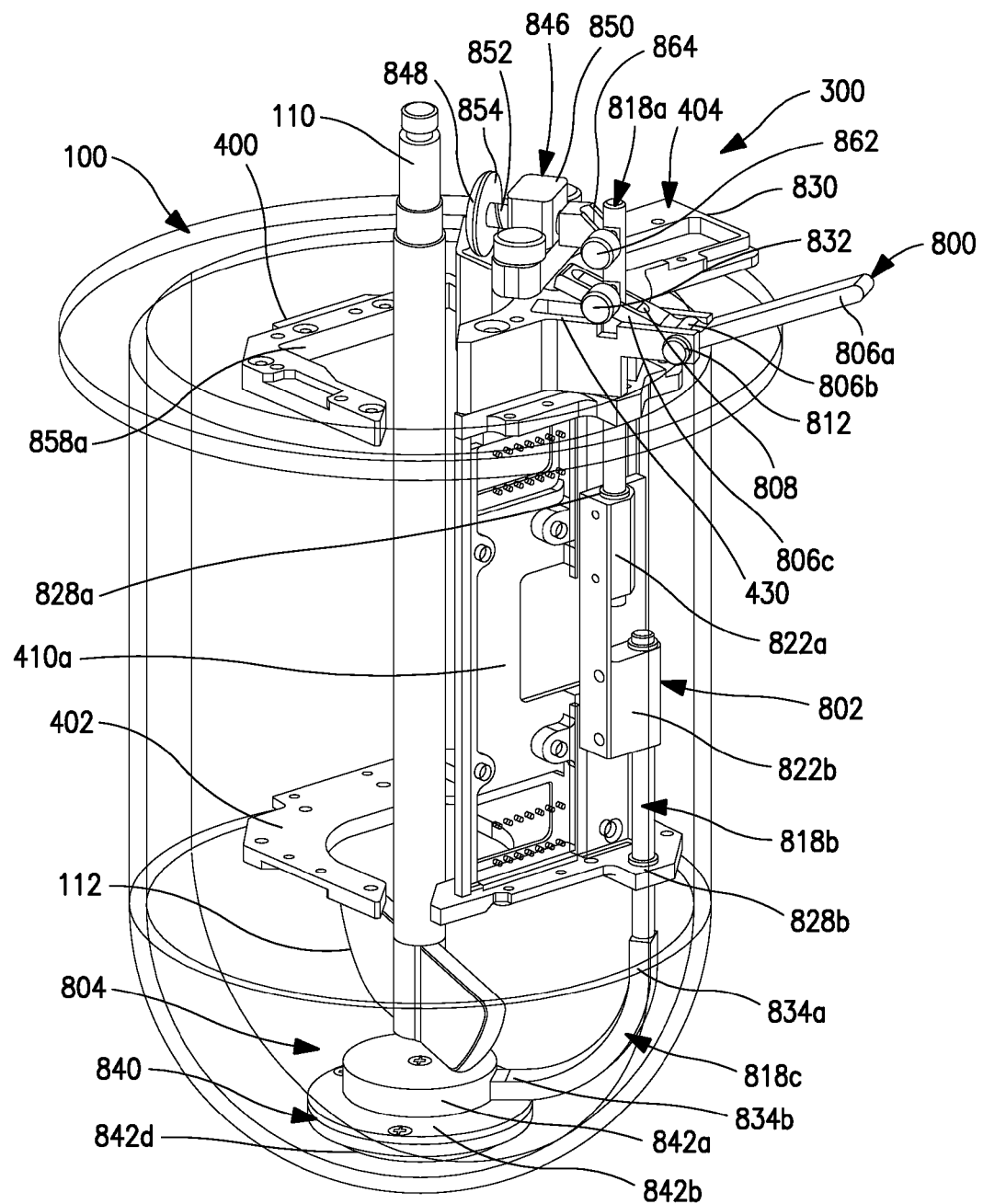
FIG. 8B is a top perspective view of an assembled height measurement system and basket wobble lifter of the example measurement device of FIG. 8A disposed within a vessel.

FIG. 8A and FIG. 8B illustrate a height gauge system 304 of the measurement device 300. In FIG. 8A, an exploded top perspective view of components relating to an example height gauge system 304 is shown. In FIG. 8B, a top perspective view of an assembled example height gauge system 304 installed in a vessel 100 is shown. The height gauge system 304 generally includes a lever 800, a linearly displaceable arm 802, and a target pad 804. In the example shown, the linearly displaceable arm 802 is a vertical plunger. The lever 800 may be used to raise or lower the plunger 802, which in turn raises or lowers the target pad 804. As seen in FIGS. 8A-B, the target pad 804 is positioned below the bottom of the shaft 110 in the hemispherical lower end 108 of the vessel 100. The target pad 804 is used to measure the distance from the bottom of the vessel 100 to the bottom a paddle 112 or basket attached to the shaft 110. In a neutral position, the target pad 804 rests on the bottom of the vessel 100. As described in further detail below, actuating the lever 800 in a downward direction raises the plunger 802 and target pad 804 in an upward direction. The plunger 802 and target pad 804 will continue in an upward direction until the target pad 804 impacts the bottom of the paddle 112 or basket of the shaft 110. When the lever 800 is released from a downwardly actuated position, gravity will return the target pad 804 to the bottom of the vessel 100 and the plunger 802 and lever 800 will return to a neutral position. Based on the distance traveled by the target pad 804 from a point of maximum displacement to the bottom of the vessel 100, the measurement device 300 can determine the height of the shaft 110 within the vessel.

In the example height gauge system 604 shown in FIG. 8A and FIG. 8B, the lever 800 of the height gauge system includes a pushing portion 806a, a pivot point 806b, and a biasing portion 806c. As shown, the pushing portion 806a and the biasing portion 806c are angled relative to the pivot point 806b. The biasing portion 806c includes a slit 808 formed along the length of the biasing portion 806c. The pivot point 806b includes a bore 810 formed through the side of the lever 800. The lever 800 is positioned in the channel 430 between the two projections 428 of the upper mounting frame 404 and attached to the projections via a pin 812 that passes through the bore 810 formed through the pivot point 806b of the lever and a bore 814 formed through each of the projections. The pin 812 is secured via an e-style retaining ring 816a attached to a groove 816b formed around the circumference of the pin 812. As seen in the assembled configuration shown in FIG. 8B, the pushing portion 806a and the biasing portion 806c of the lever 800 are both angled in an upward direction relative to the upper mounting piece 404.

The plunger 802 of the example height gauge system 304 of FIG. 8A and FIG. 8B includes a plunger body 818a, a linear upper plunger rod 818b, a linear lower plunger rod 818c, and an arcuate target rod 818d. The upper plunger rod 818b is disposed within a bore 820a formed through an upper portion 822a of the plunger body 818a and secured by two e-style retaining rings 824a attached to grooves 824b formed around the circumference of the upper plunger rod 818b. The upper plunger rod 818b also passes through a bore 420 formed in the upper retainer frame 400. A sleeve 828a to facilitate movement of the upper plunger rod 818b is also disposed within the bore 420 of the upper retainer frame 400 between the upper plunger rod 818b and the bore 420. An upper portion 830 of the upper plunger rod 818b extends through the slit 808 of the biasing portion 806c of the lever 800. As seen in FIG. 8B, a mechanical stop 832 is secured to the upper portion 830 of the upper plunger rod 818b at a point just above the slit 808 of the biasing portion 806c of the lever 800. In the example height gauge system 304 shown in FIG. 8B, the mechanical stop 832 is knob 832a having a pin 832b that passes through the upper portion 830 of the upper plunger rod 818b. Accordingly, as the pushing portion 806a of the lever 800 is actuated in a downward direction, the biasing portion 806c of the lever 800 is actuated in an upwards direction via the pivot point 806b and impacts the mechanical stop 832 raising the plunger 802 in an upward direction as well. When the lever 800 is released, gravity draws the plunger 802 in a downward direction, and the mechanical stop 832 pushes the biasing portion in a downward direction until the arm returns to a neutral position.

Like the upper plunger rod 818b, the lower plunger rod 818c is disposed within a bore 820b formed through a lower portion 822b of the plunger body 818a. The lower plunger rod 818c is also secured by two e-style retaining rings 826a attached to grooves 826b formed around the circumference of the lower plunger rod 818c. The lower plunger rod 818c likewise passes through a sleeve 828b disposed within a bore 422 of the lower retaining frame 402. The target rod 818d is attached to the bottom of the lower plunger rod 818c at a first end 834a and arcs towards the center and the bottom vessel 100 as shown in FIG. 8B. The target pad 804 is attached to the target rod 818d at a second end 834b opposite the first end 834a of the target rod 818d. As seen in the assembled configuration of FIG. 8B, the target pad 804 rests at the bottom and near the center of the vessel 100 below the paddle 112 of the shaft 110.

The plunger body 818a of the example height gauge system 304 of FIG. 8A and FIG. 8B also includes an inward-facing groove 836 that holds the vertical magnetic strip 482a used to determine the height of the target pad 804. A linear encoder 482b is mounted to the exterior surface of the third PCB 412c. The linear encoder 482b interfaces with the magnetic strip 482a through the window 450 of the PCB cover 416, which exposes the linear encoder 482b to the magnetic strip 482a. As the plunger 802 and magnetic strip 482a move upward and downward, the linear encoder 482b senses the linear displacement of the plunger 802 and generates a signal corresponding to the position of the plunger 802. A calculation unit may then calculate the height of the target pad 804 based on the measured position of the plunger 802.

In the example height gauge system 304 of FIG. 8A and FIG. 8B, the target pad 804 includes a ball bearing 838 housed within a target housing 840. The target housing 840 includes a housing cap 842a, a retaining ring 842b, a mounting cap 842c, and a base 842d. As can be seen from FIG. 8A, the retaining ring 842b is secured to the base 842d, and the housing cap 842a and mounting cap 842c are secured to the target rod 818d through the center of the retaining ring 842b. The ball bearing 838 is held within a recess 844a formed in the bottom of the base 842d. The mounting cap 842c also secures the ball bearing 838 in the recess 844a of the base 842d as can be seen from FIG. 8A. The recess 844a also includes an aperture 844b through which a portion of the ball bearing 838 extends to contact the bottom of the vessel 100 when the measurement device 300 is installed within the vessel. Accordingly, when the measurement device 300 is installed within a vessel 100, the ball bearing 838 of the target pad 804 may float within the recess 844a of the base 842d, extend through the aperture 844b at the bottom of the base 844b, and come to rest at the bottom of the vessel 100. A suitable ball bearing, for example, may be 8 (eight) millimeters in diameter and made of stainless steel.

Enclosing the ball bearing 838 in a target pad 804 is an improvement over known systems whereby an unrestrained and free-floating ball bearing is placed within a vessel. Operators may have difficulty retrieving unrestrained ball bearings once testing is complete. Accordingly, placing the ball bearing 838 within a recess 844a of a target pad 804, as shown in FIGS. 8A-B, allows for quick and easy retrieval once testing is complete.

Also shown in FIG. 8A and FIG. 8B is the basket wobble lifter 306 that may be used to calculate basket wobble as discussed further below. The basket wobble lifter 306 includes: a spring-biased pad 848; a body 850; a pin 852; a spring 854; a clip 856; and a sloped lifter portion 858. The spring-biased pad 848 is connected to the clip 856 by the pin 852 that passes through a bore of the body 850 of the basket wobble lifter 306. The spring 854 wraps around the pin 852 and biases the pad towards the shaft 110. The clip 856 is designed to receive the upper plunger rod 818b of the height gauge system 304. As seen in FIG. 8B, the upper plunger rod 818b may be positioned between the sloped lifter portion 858 of the clip 856. A mechanical stop 862 may be positioned above the lifter portion 858 also passing through the upper portion 830 of the upper plunger rod 818b.

As can be seen from FIG. 8B, when the pad 848 moves towards the upper plunger rod 818b, the lifter portion 858 comes into contact with the mechanical stop 862 passing through the upper plunger rod 818b like mechanical stop 832. As the lifter portion 858 is further pushed towards the upper plunger rod 818b, the upper plunger rod 818b will slide up the slope 864 of the lifter portion in an upwards direction. Similarly, when the pad 848 and lifter portion 858 move away from the upper plunger rod 818b, the upper plunger rod 818b will slide back down the slope 864 of the lifter portion 858 in a downwards direction. This upwards and downwards movement may be sensed by the linear encoder 482b as explained above. Further, this upwards and downwards movement caused by the basket wobble lifter 306 may be used to calculate basket wobble as explained further below.

Test Routine

Referring now to FIGS. 9A-G, flow diagrams of a test routine using the example measurement device 300 and various subroutines of the test routine are shown. The test routine may be performed to obtain measurements relating to the shaft 110 disposed within a vessel 100 using the measurement device 300 described above. Based on the measurements obtained from the measurement device 300, a calculation unit may calculate and determine various parameters relating to the shaft 110 and/or vessel 100. The measurement device 300 may be connected to a data collection and control unit, such as a desktop computer or hand-held computer, via a communication bus 308 (FIGS. 3A-B). The data collection and control unit may include an executable software program that walks an operator through a testing routing and prompts the operator at various stages of the testing routine. A display of the data collection and control unit may present various screen displays to the operator with instructions on how to prepare and operate the measurement device 300. The screen displays may also present to the operator the measurements obtained from the measurement device 300.

Figure 9A:
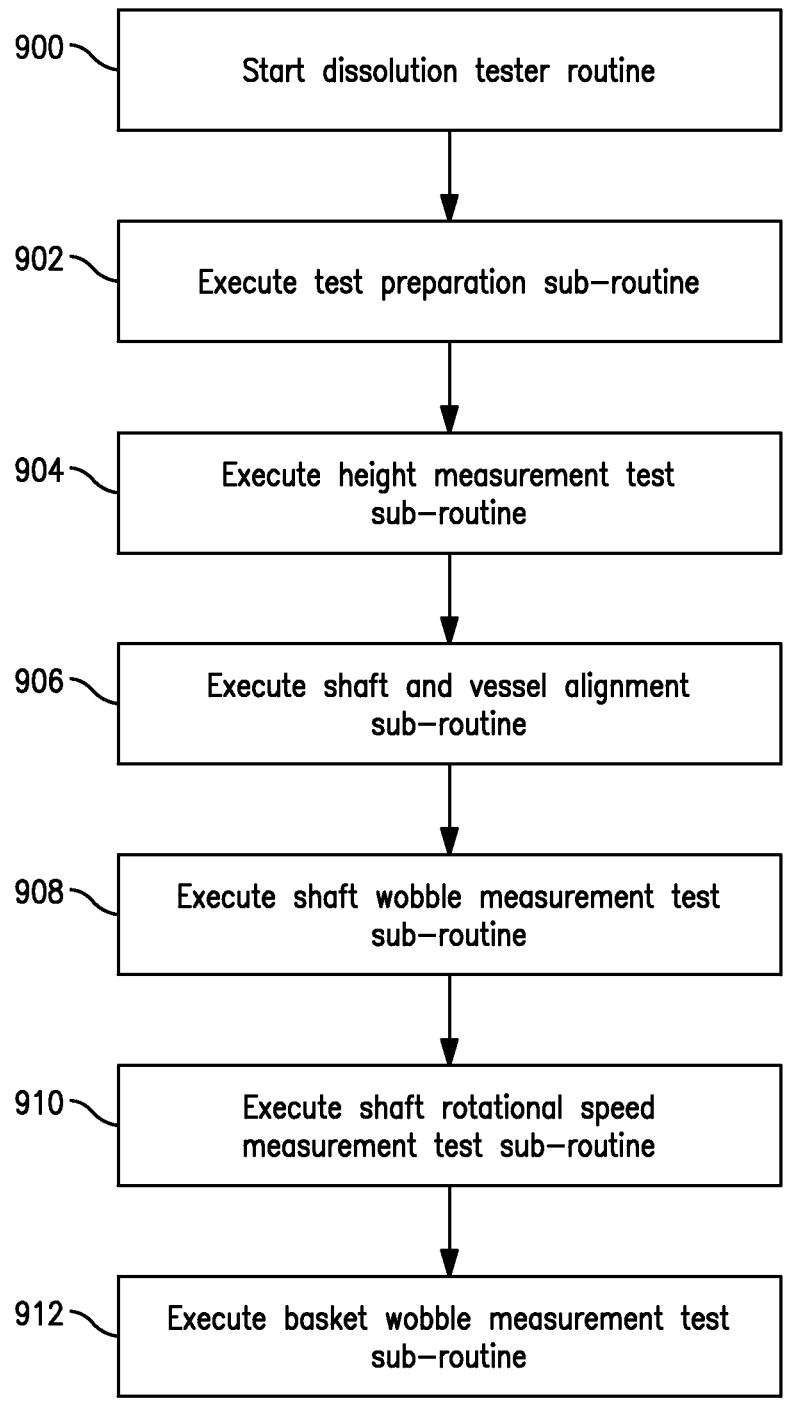
FIG. 9A is a flow chart showing an example testing routine used to measure various shaft and vessel parameters using the measurement device described herein.

As seen in FIG. 9A, the testing routine 900 may include the following subroutines: a test preparation subroutine 902; a shaft height measurement subroutine 904; a shaft and vessel alignment subroutine 906; a shaft wobble measurement subroutine 908; a rotational speed measurement subroutine 910; and a basket or paddle wobble measurement subroutine 912.

Figure 9B:
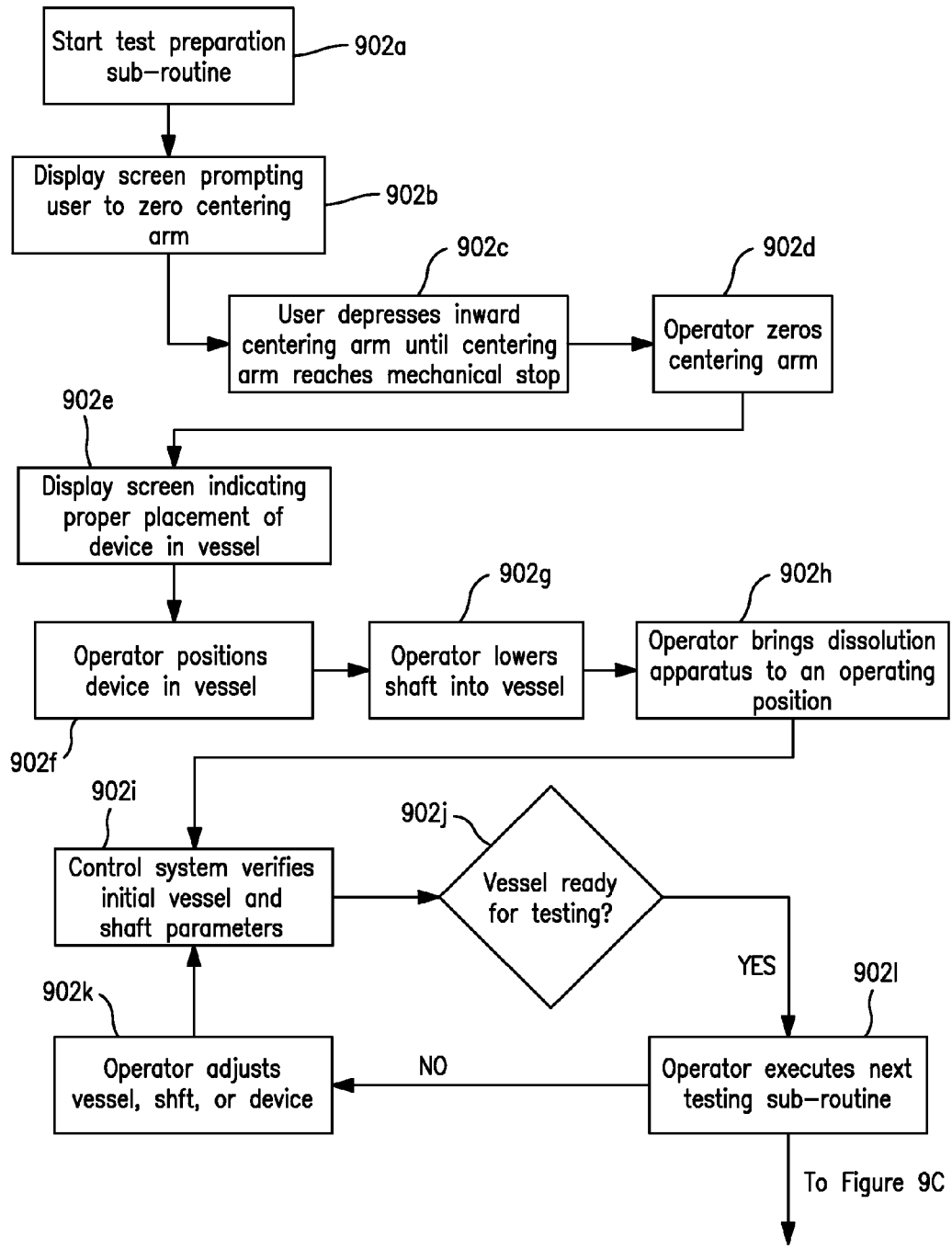
FIGS. 9B-9G are flow charts of example subroutines for the testing routine of FIG. 9A.

Referring to FIG. 9B, a flow diagram for a test preparation subroutine 902 for an example testing routine is shown. The test preparation subroutine is started at step 902*a*. A screen display prompts to an operator to prepare the measurement device 300 for testing by zeroing the centering arm at step 902*b*. The operator depresses the centering arm inward until the centering arm reaches a mechanical stop at step 902*c*. While keeping the centering arm depressed, the operator selects a button to obtain an initial reference position for the centering arm at step 902*d*.

Having obtained an initial reference position for the centering arm, a screen display may illustrate the proper placement of the measurement device 300 in a vessel at step 902*e*, and an operator may then insert the measurement device 300 into the vessel at step 902*f*. Next, the shaft is inserted into the vessel at step 902*g*, and the operator brings the dissolution apparatus to an operating position at step 902*h*. In order to ensure proper placement, various parameters relating to the measurement device 300, such as vessel verticality, may be checked and verified at step 902*i*. The operator determines if the vessel is ready for testing based on the initial shaft and vessel parameters at step 902*j*, and the operator may adjust the shaft and vessel at step 902*k* if the shaft and vessel are not ready for testing, and repeats the test starting at step 902*i*. If the shaft and vessel are ready for testing, the operator may proceed to the first testing subroutine at step 902*l*.

Figure 9C:
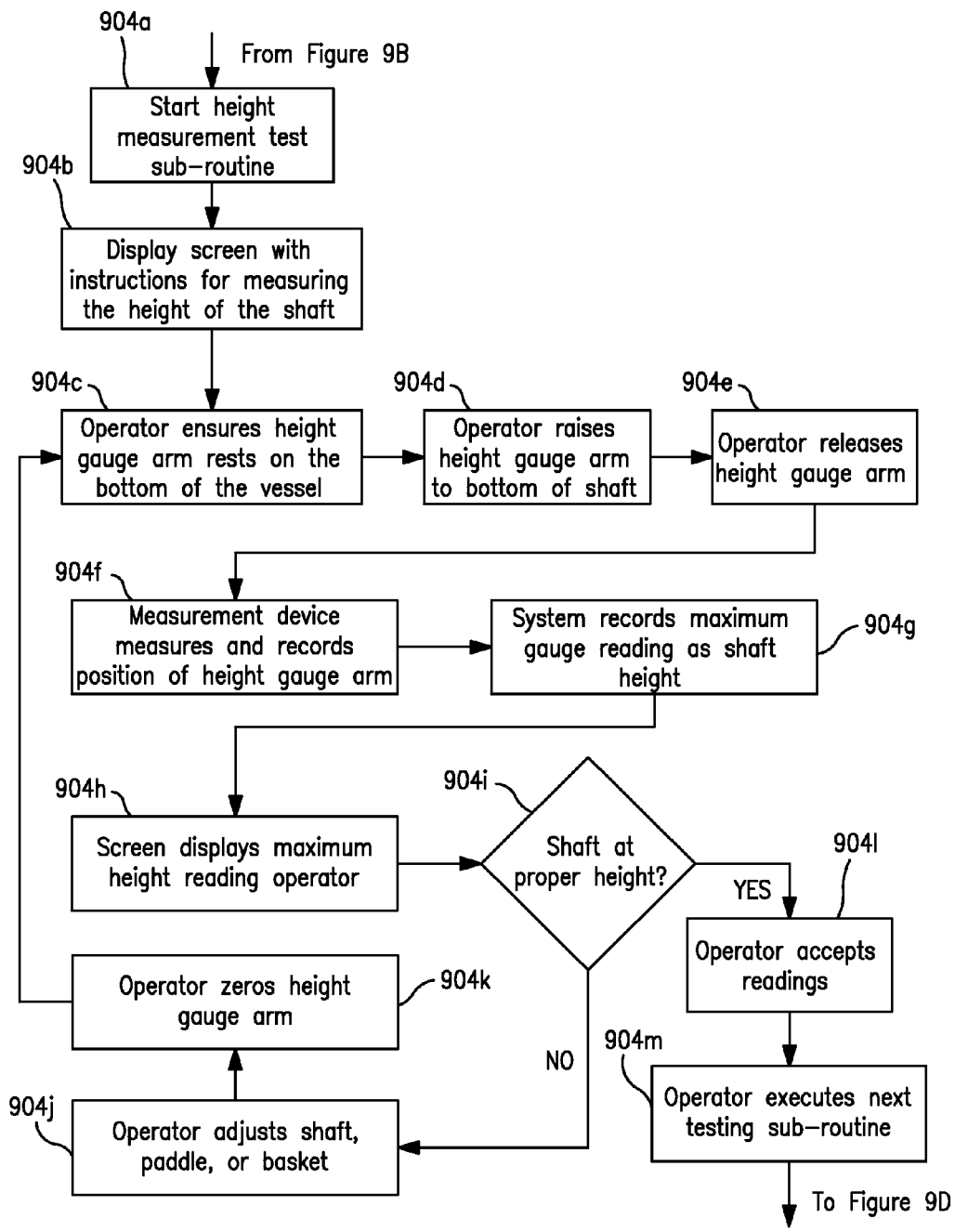

In an example testing routine, the first test to follow the preparation subroutine may be the shaft height measurement subroutine. The shaft height measurement subroutine measures the distance from the bottom of the shaft paddle or basket to the bottom of the vessel. FIG. 9C shows a flow chart for an example shaft height measurement subroutine 904. The shaft height measurement subroutine begins at step 904*a*. At step 904*b*, a screen displays instructions to the operator regarding the procedure for measuring shaft height. At step 904*c*, the operator ensures the target pad of the height gauge system rests on the bottom of the vessel. Then, the operator raises the target pad up to the bottom of the shaft paddle or basket at step 904*d*. Next, the operator releases the lever of the height gauge system so that the target pad returns to the bottom of the vessel at step 904*e*.

The data collection and control unit measures and records the maximum displacement of the target pad at step 904*f* and step 904*g* respectively. A screen then displays the readings to the operator at step 904*h*. The operator then determines whether the paddle or basket is at the desired height at step 904*i*, and if not, adjusts the shaft, paddle, or basket at step 904*j*, zeros the recorded height at step 904*k*, and repeats the test starting with step 904*c*. If the recorded height is acceptable, the operator may accept the reading at step 904*l* and proceed to the next test of the testing routine at step 904*m*.

Figure 9D:
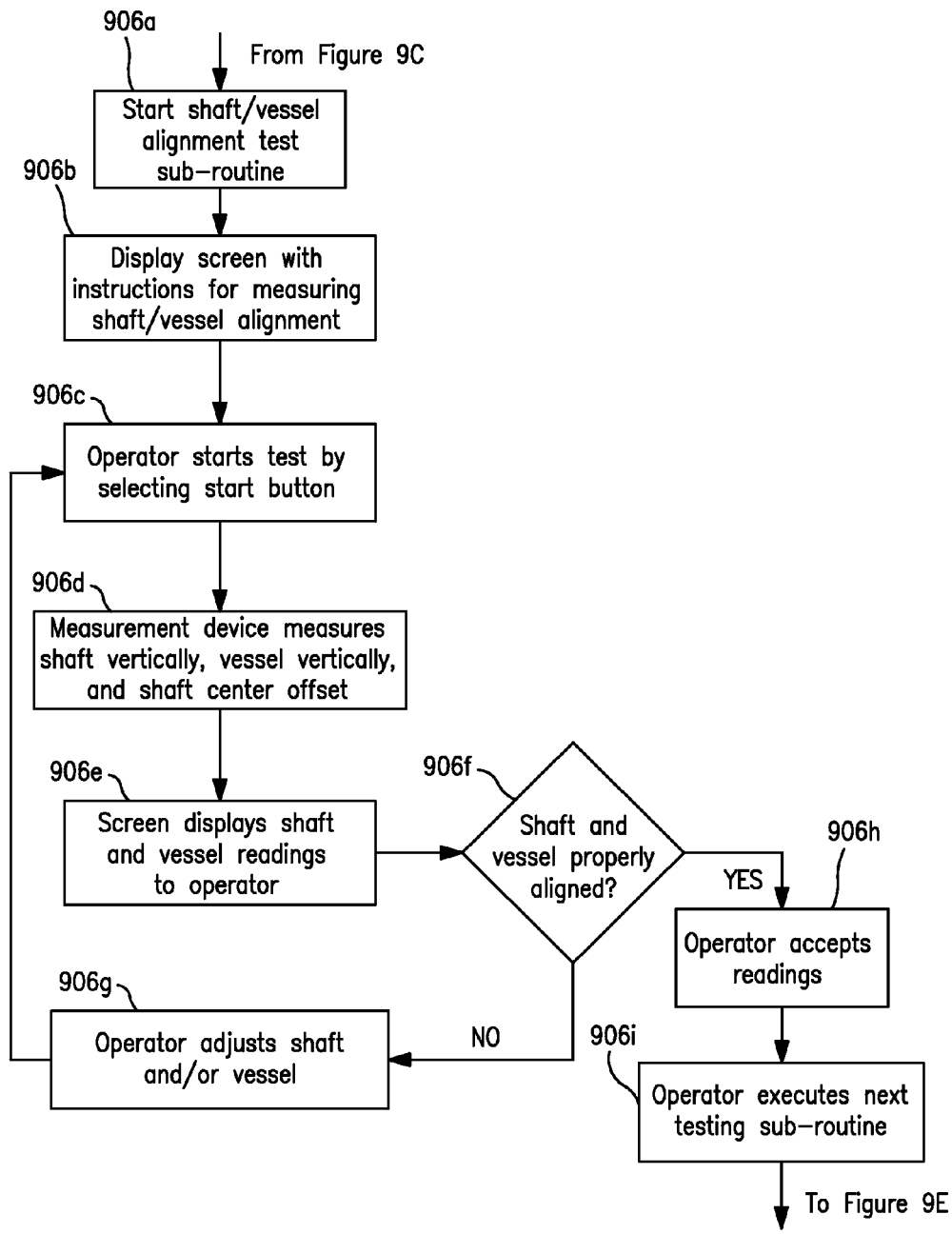

A shaft and vessel alignment subroutine may follow the shaft height measurement subroutine in an example testing routine. The shaft and vessel alignment subroutine may simultaneously execute three measurement tests to determine vessel verticality, shaft verticality, and shaft offset from the center of the vessel. FIG. 9D shows a flow chart for an example shaft and vessel alignment subroutine 906. The shaft and vessel alignment test starts at step 906*a*. At step 906*b*, a screen displays instructions for measuring shaft verticality, vessel verticality, and shaft center offset, and the operator starts the test by selecting a start button at step 906*c*.

Once the test has started, the measurement device 300 measures the vessel verticality, shaft verticality, and shaft center offset via the inclinometer and optical micrometers at step 906*d* according to the method described above. Next, the data collection and control unit obtains the readings from the measurement device 300 and displays the readings to the operator at step 906*e*. The operator then determines if the shaft verticality, vessel verticality, and shaft center offset are within acceptable alignment ranges at step 906*f*. If not, the operator may adjust the shaft and/or vessel as necessary at step 906*g* and repeat the test by returning to step 906*c*. Once the shaft and vessel are appropriately positioned and aligned, an operator may accept the readings at step 906*h* and proceed to the next test subroutine at step 906*i*.

Figure 9E:
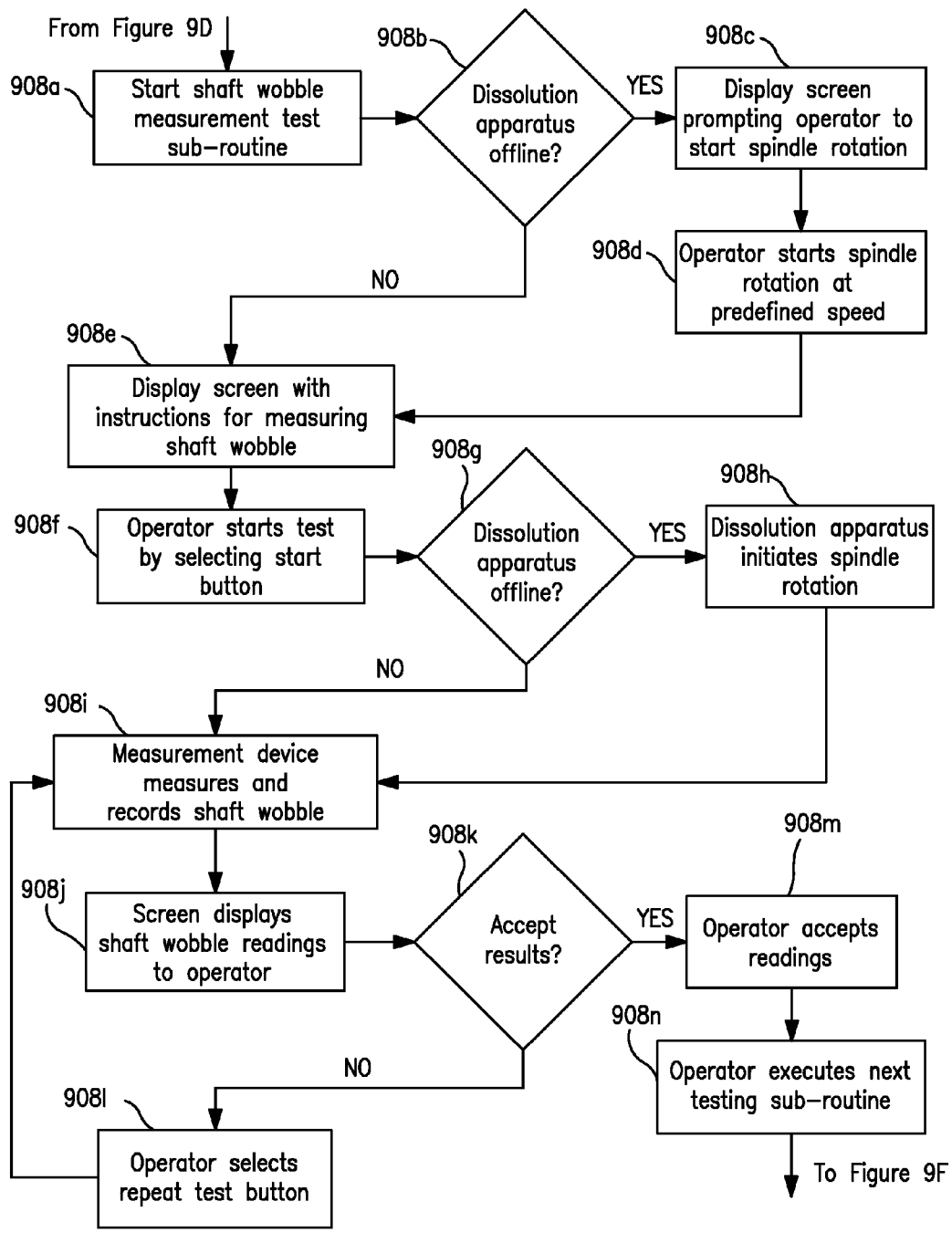

A shaft wobble measurement subroutine may follow the shaft and vessel alignment subroutine in an example testing routine. The shaft wobble measurement subroutine may, for example, measure the wobble of the shaft two millimeters above the shaft paddle or basket for 20 (twenty) seconds at a rotational speed of 20 (twenty) RPM. FIG. 9E shows a flow chart for an example shaft wobble measurement subroutine 908. The shaft wobble measurement subroutine 908 begins at step 908*a*. The data collection and control system determines if the dissolution apparatus is offline at step 908*b*, and if so, displays a screen to the operator prompting the operator to activate the spindle to rotate the shaft and set an appropriate rotational speed at step 908*c*. The operator may appropriately set the rotational speed and initiate the rotation of the shaft at step 908*d*. If the dissolution apparatus is online, a screen displays a start button at step 908*e*, and the operator may select the button to start the shaft wobble measurement test at step 908*f*. If the dissolution apparatus was already online, as determined at step 908*g*, the spindle motors begin rotating automatically at step 908*h* once the operator begins the test.

During the 20 (twenty) second period in which the shaft rotates, the measurement device 300 measures the wobble of the shaft with the optical micrometers according to the method described above at step 908*i*. At the end of the 20 (twenty) second testing period, the data collection and control unit displays the measurement readings to the operator at step 908*j*. The operator determines if the shaft wobble measurements are acceptable at step 908*k*. If not, an operator may repeat the test at step 908*l* and return to 908*i* to obtain new shaft wobble measurements. An operator may accept the results at step 908*m*, and proceed to the next test subroutine at step 908*n*.

Figure 9F:
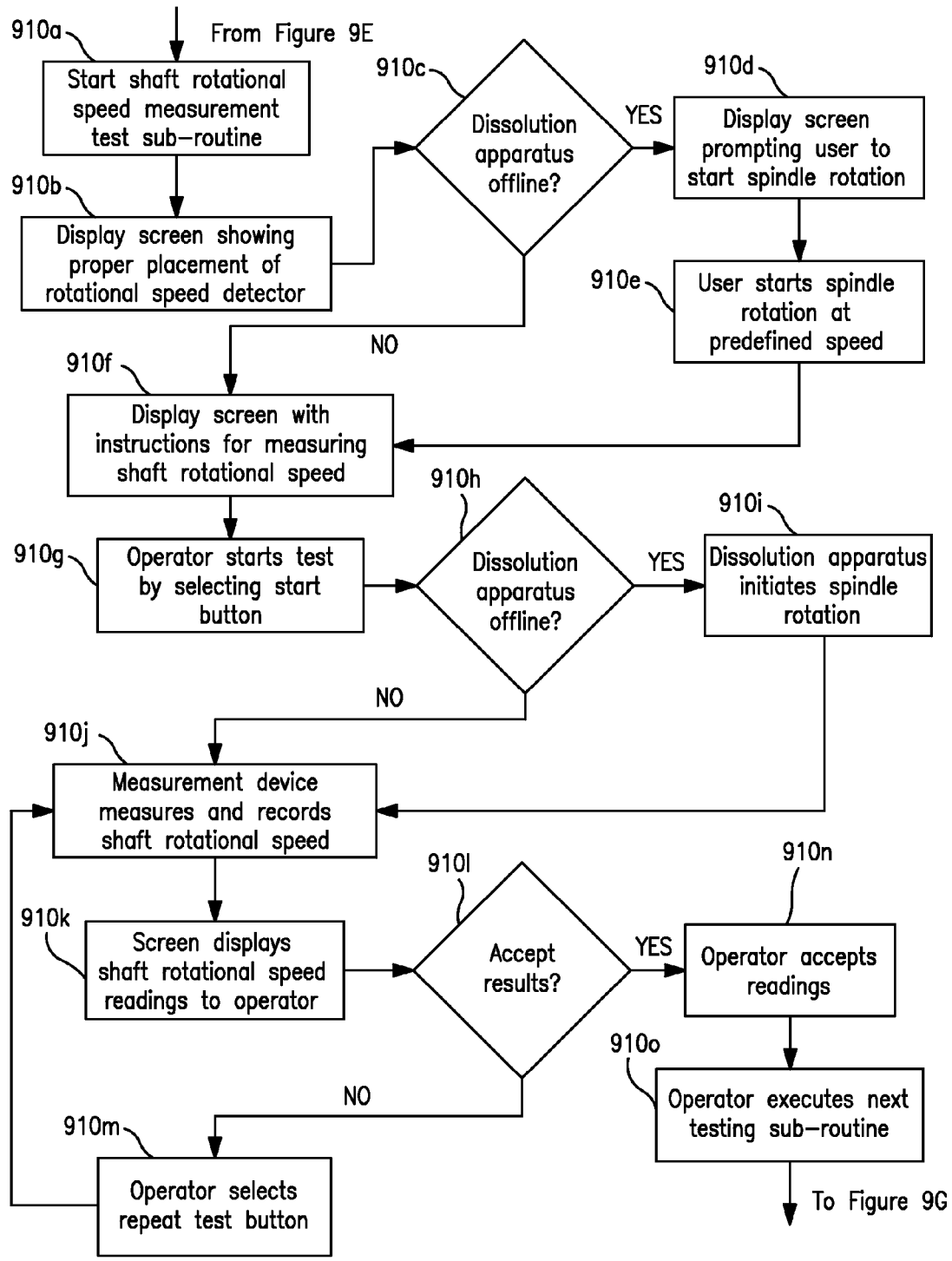

An example testing routine may follow the shaft wobble measurement subroutine with a rotational speed measurement subroutine. The rotational speed measurement subroutine may measure the rotations-per-minute of the shaft for a period of 10 (ten) seconds at predefined rotational speed, such as 50 RPM. FIG. 9F shows a flow chart of an example rotational speed measurement subroutine 910. The rotational speed measurement subroutine begins at step 910a. A screen displays the proper placement of the RPM detection magnet to the operator at step 910b. Similar to the shaft wobble test, the data collection and control unit determines if the dissolution apparatus is offline at step 910c and, if so, prompts the operator to start the spindle rotation at the desired rotational speed at step 910d. The operator sets the appropriate rotational speed and initiates the rotation of the shaft at step 910e. If the dissolution apparatus is online, as determined at step 910f, a screen displays the rotational speed measurement screen at step 910g. The operator may select a button on the display screen to begin the test at step 910h. If the dissolution apparatus was already online, rotation starts automatically at step 910i once the operator begins the test. During the 10 (ten) second testing period, the measurement device 300 measures the rotational speed of the shaft according to the method described above at step 910j. At the end of the testing period, the data collection and control unit displays the measurements to the operator at step 910k. An operator may determine if the results are acceptable at step 910l and repeat the test at step 910m. Alternatively, an operator may accept the results at step 910n, and proceed to the next test as step 910o.

Figure 9G:
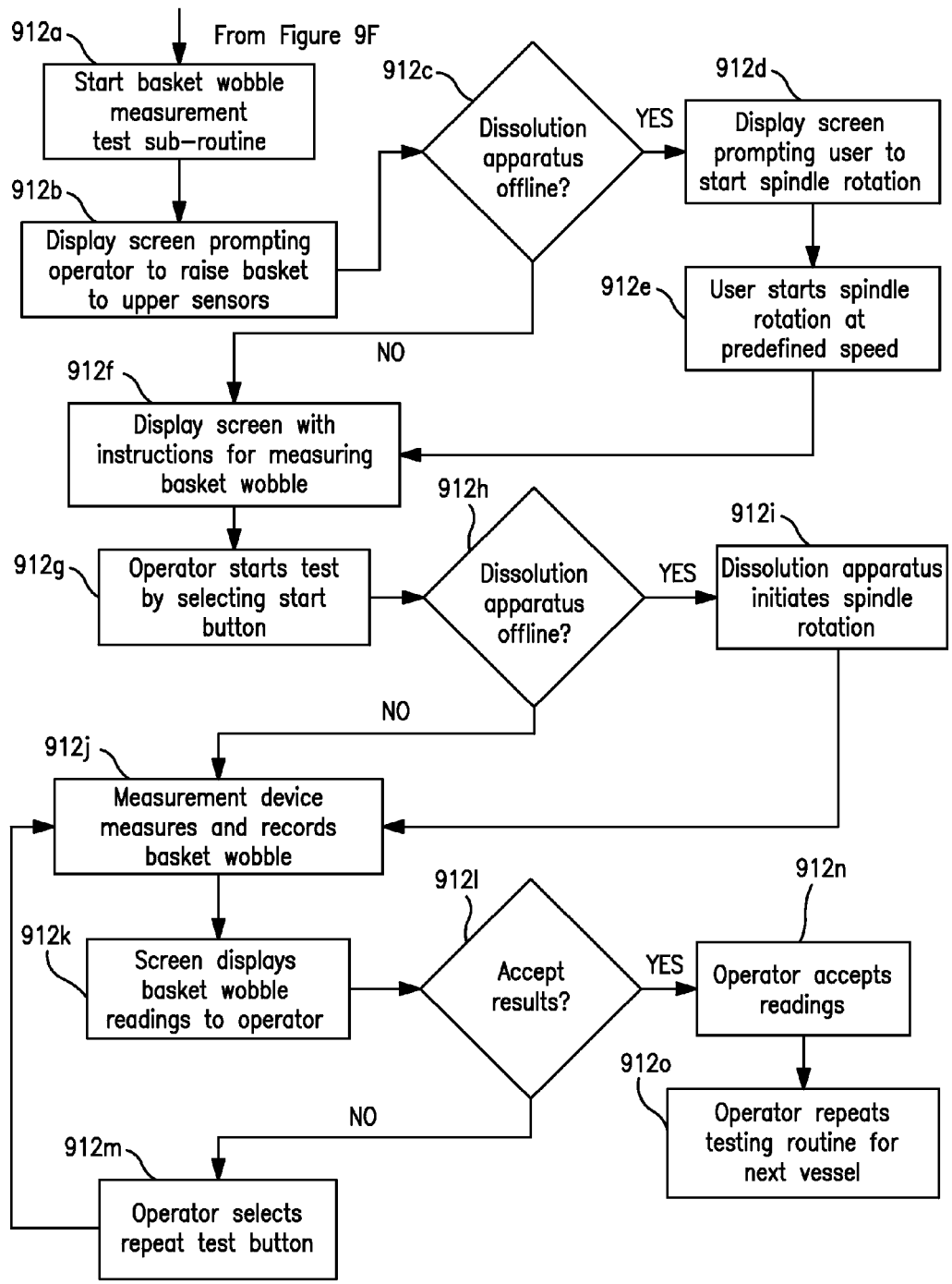

A basket wobble measurement subroutine may be the final subroutine in an example testing routine. The basket wobble measurement subroutine measures the wobble of the bottom rim of a shaft basket for a period of, for example, 20 (twenty) seconds at a predefined rotational speed, such as 20 (twenty) RPM. FIG. 9G shows a flow chart for an example basket wobble measurement subroutine 912. The basket wobble measurement subroutine begins at step 912a. At step 912b, a screen display prompts the operator to bring the lower rim of the shaft basket to the upper set of optical micrometers. Next, the data collection and control unit determines if the dissolution apparatus is offline at step 912c and, if so, prompts the operator to start the spindle rotation at a predefined rotational speed at step 912d. The operator sets an appropriate rotational speed and initiates the rotation of the shaft at step 912e. Next, a screen displays the basket wobble measurement screen at step 912f, and an operator selects begins the basket wobble measurement subroutine at step 912g. If the dissolution apparatus was already online, as determined at step 912h, the rotation of the spindle starts automatically at step 912i. During the 20 (twenty) second testing period, the measurement device 300 measures the shaft basket wobble according to the method set forth above at step 912j. At the end of the testing period, the data collection and control unit displays the measurements to the operator at step 912k. An operator may determine if the results are acceptable at step 912l and repeat test button at step 912m returning to step 912j. The operator may accept the readings at step 912n. Having completed a full testing routine for one vessel, the operator may retrieve the measurement device 300 from the vessel and repeat the testing routine for another vessel at step 912o.

The testing routine described above sets forth the various tests and subroutine for a single vessel. An operator would execute the dissolution testing routine of FIG. 9A for each vessel of a dissolution apparatus.

Calculations

Example methods of calculating the shaft and vessel alignment parameters using the inclinometer, optical micrometers, and rotational speed indicator will now be discussed. In particular, the example approaches for determining the shaft center offset, vessel verticality, shaft verticality, paddle/basket height, shaft wobble, and basket wobble are explained below. Those skilled in the art will understand that the calculations in this example may be performed by firmware residing on the measurement device 300 itself, by software residing at an external calculation unit, or a combination of both firmware at the measurement device 300 and software at an external calculation unit.

Figure 10:
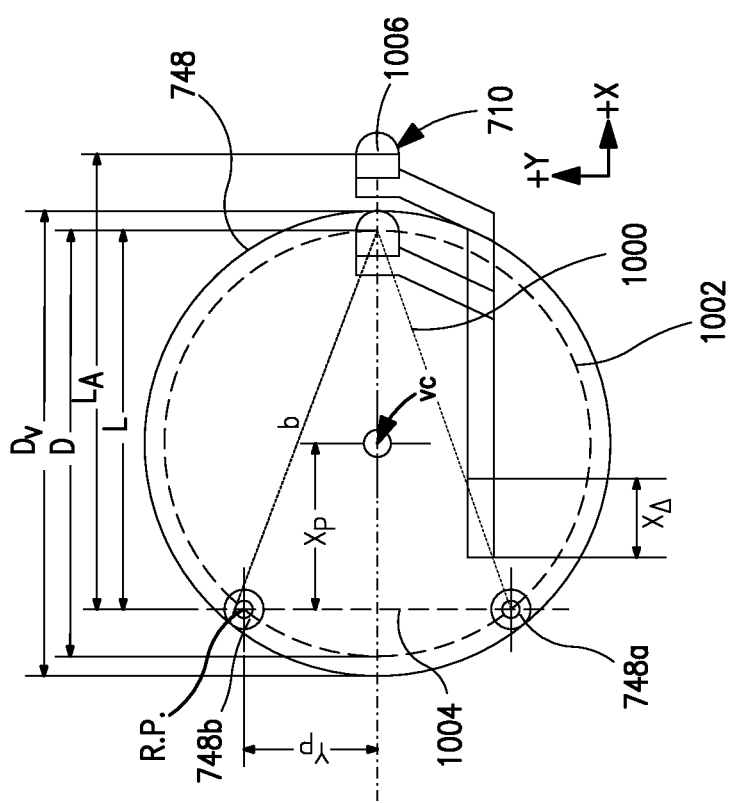
FIG. 10 is a top schematic view of a vessel and a centering arm illustrating the measurements that may be used to calculate the diameter and center of the vessel.

Referring now to FIG. 10, a top schematic diagram of a vessel 100 and a centering arm 700 is shown. FIG. 10 also includes the measurement values that may be used to calculate the diameter $D_V$ and center of the vessel VC. The calculation of the vessel diameter $D_V$ yields a reference value used for calculations regarding the vessel center VC and shaft center. In the example measurement device 300 described herein, the law of sines may be used to determine the center VC of the vessel 100. As seen in FIG. 10, the contact points 748 and the contact point 710 at the end of the centering arm 700 form an isosceles triangle 1000, and the vessel 100 forms a circle 1002 that circumscribes the triangle 1000. The law of sines states that the ratio of the length of a side to the sine of its corresponding opposite angle is constant, i.e.

$$\frac{a}{\sin\alpha} = \frac{b}{\sin\beta} = \frac{c}{\sin\gamma} \tag{1}$$

Further, this ratio is also equal to the diameter D of the circumscribed circle 1002 of the triangle 1000:

$$D = \frac{a}{\sin\alpha} \tag{2}$$

Accordingly, diameter D can be expressed through the area S of the triangle:

$$S = \frac{1}{2}bc\sin\alpha \tag{3}$$

$$D = \frac{abc}{2S} \tag{4}$$

In the case of the example measurement device 300, an isosceles triangle 1000 is formed between the contact points 748 and 710 having a known sides (a and b) and a height (h), yielding the following equation for the area S of the triangle having a base (c):

$$S = \frac{1}{2}ch \tag{5}$$

Since b=a in the isosceles triangle 1000 formed by the contact points 748 and 710 of the example measurement device 300, diameter D may be given by the equation:

$$D = \frac{b^2}{h} \tag{6}$$

With this equation, the measurement device 300 may be calibrated and the vessel center VC may be determined. The measurement values that may be used when calculating vessel center VC include the following:

TABLE 1

Vessel Diameter and Vessel Center Values

| Value | Description |
|---|---|
| VC | vessel center |
| RP | reference point for the vessel center (VC) measured from the center of a contact point |
| $D_{PV}$ | hypothetical diameter of a perfect vessel |
| $D_V$ | externally measured diameter of a vessel under test |
| D | diameter of the circle circumscribing the triangle formed by the center of the contact points and the centering arm contact point |
| $L_A$ | calibrated distance from the contact point axis to the end of a fully extended centering arm |
| L | calculated distance from the contact point axis to the end of a centering arm in contact with the side of a vessel under test |
| $R_B$ | Radius of a contact point |
| $X_\Delta$ | lateral displacement of the centering arm |
| $X_P$ | calculated distance from the reference point (RP) to the vessel center (VC) along the X-axis |
| $Y_P$ | known distance from the reference point (RP) to the vessel center (VC) along the Y-axis |

Before calculating the vessel center VC, the distance $L_A$ from the contact point axis 1004 to the zero position 1006 of the fully extended centering arm may be determined. To determine $L_A$, diameter D is first calculated. As discussed above, diameter D represents the diameter of the circle 1002 circumscribing the triangle 1000 formed by the contact points 748 and the center of the centering arm 700 contact point 710 where the vertices of the triangle are the centers of the contact points. Taking into account the radii of the contact points 748 and 710, diameter D is given by the equation:

$$D = D_{PV} - 2R_B \quad (7)$$

where $D_{PV}$ represents the known diameter of a hypothetical perfect vessel and $R_B$ is the known radius of the contact points. Diameter D may then be expressed using equation 6 from above, $$D = \frac{b^2}{h},$$

where $b^2 = Y_P^2 + L^2$ using the Pythagorean theorem and $h = L$:

$$D = \frac{Y_P^2 + L^2}{L} \text{ or } L^2 - DL + Y_P^2 = 0 \quad (8)$$

In this equation, $Y_P$ is a known value representing the distance between the reference point RP and the vessel center VC on the Y-axis. Thus, knowing the values of diameter D and $Y_P$, distance L, representing the distance from the contact point axis 1004 to the centering arm contact point 710, can be determined via the quadratic equation:

$$L = \frac{D + \sqrt{D^2 - 4Y_P^2}}{2} \quad (9)$$

Thus, $L_A$ may be expressed in terms of L by adding the displacement distance, $X_\Delta$, of the centering arm 700:

$$L_A = L + X_\Delta \quad (10)$$

The calibrated distance, $L_A$ may then be used when calculating the vessel diameter $D_V$ and vessel center VC based upon a reading from the linear encoder during a test routine. When calculating the diameter and center of the vessel during a test routine, distance L may first be calculated based on the direct reading of the linear encoder measurement, $X_\Delta$:

$$L = L_A - X_\Delta \quad (11)$$

As with the calibration step, a diameter D represents the diameter of a circle 1002 circumscribing the triangle 1000 formed by the contact points 748 and 710 of the measurement device 300 installed in the vessel 100 under test. Having calculated L and knowing the value for $Y_P$, diameter D may be determined by the following equation:

$$D = \frac{Y_P^2 + L^2}{L} \quad (12)$$

The entire vessel diameter $D_V$ may then be calculated by adding the radii $R_B$ of the contact points 748 and 710:

$$D_V = \frac{Y_P^2 + L^2}{L} + 2R_B \quad (13)$$

Finally, the vessel center VC on the X-axis may be calculated with the following equation:

$$X_P = L - \frac{D}{2} \quad (14)$$

Thus, the vessel center VC may then be expressed as ($X_P$, $Y_P$) where the coordinate values represent the distance of the vessel center VC from the reference point RP along the X-axis and Y-axis respectively.

Figure 11:
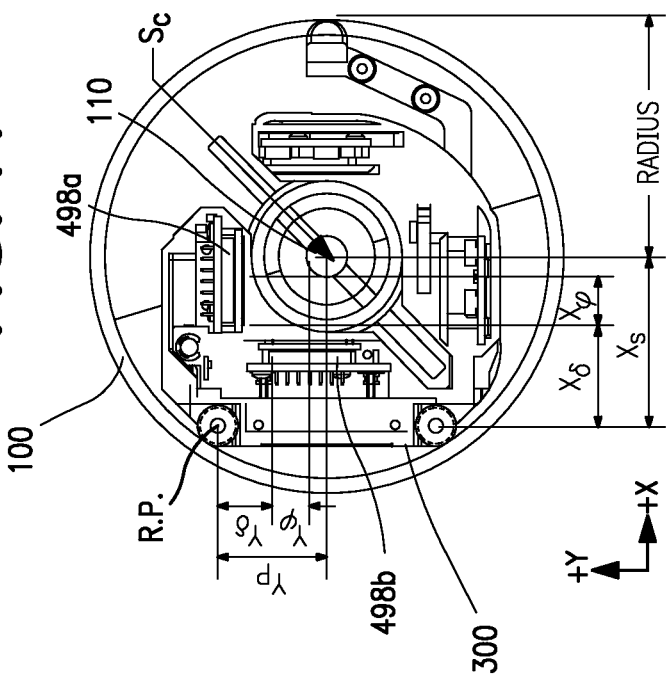
FIG. 11 is a top schematic view of a vessel, a shaft, and a measurement device illustrating the measurements that may be used to calculate the center of the shaft.

Referring now to FIG. 11, a top schematic view of a measurement device 300 and a shaft 110 are shown disposed within a vessel 100. FIG. 11 also includes the measurement values that may be used when calculating the shaft center position, which is a distance along the X-axis and Y-axis from the center of a contact point (reference point RP) to the center of the shaft SC. The measurement values that may be used when calculating vessel center include the following:

TABLE 2

Shaft Center Values

| Value | Description |
|---|---|
| VC | vessel center |
| SC | shaft center |
| RP | reference point for the shaft center (SC) measured from the center of a contact point |
| $R_B$ | radius of a contact point |
| $D_{PV}$ | hypothetical diameter of a perfect vessel |
| $R_{PV}$ | hypothetical radius of a perfect vessel |
| $X_{PV}$ | calculated distance from the reference point (RP) to the vessel center (VC) along the X-axis in a hypothetical perfect vessel |

TABLE 2-continued

Shaft Center Values

| Value | Description |
|---|---|
| $Y_{PV}$ | known distance from the reference point (RP) to the vessel center (VC) along the Y-axis in a hypothetical perfect vessel |
| $D_V$ | calculated diameter of a vessel under test |
| $D_{PS}$ | diameter of a hypothetical perfect shaft |
| $R_{PS}$ | radius of a hypothetical perfect shaft |
| $X_\delta$ | distance along the X-axis from the reference point (RP) to the last pixel in the linear sensor array |
| $Y_\delta$ | distance along the Y-axis from the reference point (RP) to the last pixel in the linear sensor array |
| $X_\phi$ | distance along the X-axis from the first pixel of the linear sensor array to the shaft edge |
| $Y_\phi$ | distance along the Y-axis from the first pixel of the linear sensor array to the shaft edge |
| $X_S$ | distance between the reference point (RP) and the shaft edge along the X-axis |
| $Y_S$ | distance between the reference point (RP) and the shaft edge along the Y-axis |
| $D_S$ | shaft diameter |
| $X_C$ | distance between the reference point (RP) and the shaft center (SC) along the X-axis |
| $Y_C$ | distance between the reference point (RP) and the shaft center (SC) along the Y-axis |

Assuming the vessel 100 and shaft 110 are perfectly aligned, using the diameter $D_{PV}$ of a perfect vessel, the diameter $D_{PS}$ of a perfect shaft, and the known value of $Y_{PV}$, the distance $X_{PV}$ from the reference point RP to the shaft center SC along the X-axis in a hypothetical perfect vessel may be determined by the following equation:

$$X_{PV} = \sqrt{(R_{PV} - R_B)^2 - Y_{PV}^2} \quad (15)$$

where $R_{PV}$ is the radius of the perfect vessel, $R_B$ is the radius of the contact points, and $Y_{PV}$ is the known distance from the reference point RP to the perfect vessel center VC along the Y-axis. In the instance where the vessel 100 and the shaft 110 are perfectly aligned, the shaft center SC will be the same as the vessel center VC.

When determining the shaft center SC, the distances $X_\delta$ and $Y_\delta$ along the X-axis an Y-axis respectively from the reference point RP to the last pixel in the linear sensor arrays 498 are calculated according to the equations:

$$X_\delta = (X_{PV} - X_\phi - R_{PS}) \quad (16)$$

$$Y_\delta = (Y_{PV} - Y_\phi + R_{PS}) \quad (17)$$

where $X_{PV}$ and $Y_{PV}$ respectively represent the distance along the X-axis and Y-axis from the reference point RP to the center VC of a perfect vessel, $X_\phi$ and $Y_\phi$ respectively represent the distance along the X-axis and Y-axis to the first pixel in the linear sensor array 498, and $R_{PS}$ is the radius of a perfect shaft. These values may then be used to determine the distance $X_S$ and $Y_S$ along the X-axis and Y-axis respectively from the reference point RP to the edge of the shaft:

$$X_S = X_\delta + X_\phi \quad (18)$$

$$Y_S = Y_\delta + Y_\phi \quad (19)$$

Finally, an actual shaft diameter $D_S$ or a default shaft diameter may be used to determine the distance $X_C$ and $Y_C$ along the X-axis and Y-axis respectively from the reference point RP to the shaft center SC. Where measurement devices include an upper pair and a lower pair of measurement units, the values discussed above may be calculated for both the upper and lower pair for use in determining shaft verticality as discussed below.

Referring now to FIG. 12, another top schematic view of a measurement device 300 and a shaft 110 are shown disposed within a vessel 100. FIG. 12 also includes the measurements that may be used when calculating the shaft center SC offset relative to the vessel center VC. The measurement values that may be used when calculating shaft center SC offset include the following:

TABLE 3

Shaft Center Offset Values

| Value | Description |
|---|---|
| VC | vessel center |
| SC | shaft center |
| $X_P$ | calculated distance from reference point (RP) to vessel center (VC) along the X-axis |
| $Y_P$ | known distance from reference point (RP) to vessel center (VC) along the Y-axis |
| $X_{C1}$ | calculated distance between the reference point (RP) and the shaft center (SC) along the X-axis for an upper pair of sensors |
| $Y_{C1}$ | calculated distance between the reference point (RP) and the shaft center (SC) along the Y-axis for an upper pair of sensors |
| $X_{C2}$ | calculated distance between the reference point (RP) and the shaft center (SC) along the X-axis for a lower pair of sensors |
| $Y_{C2}$ | calculated distance between the reference point (RP) and the shaft center (SC) along the Y-axis for a lower pair of sensors |
| $C_1$ | distance between the vessel center (VC) and the shaft center (SC) at the top of the shaft |
| $C_2$ | distance between the vessel center (VC) and the shaft center (SC) at the bottom of the shaft |

As seen in FIG. 12, the distance $(X_P, Y_P)$ from the reference point RP to the vessel center VC, the distance $(X_{C1}, Y_{C1})$ between the reference point and the top of the shaft center SC, and the distance $(X_{C2}, Y_{C2})$ between the reference point and the bottom of the shaft 110 may be calculated using the equations set forth above. Having obtained these values, the distance $C_1$ and $C_2$ between the vessel center VC and the shaft center SC (i.e., shaft center offset) at the top and bottom of the shaft 110 respectively may be calculated using the Pythagorean theorem:

$$C_1 = \sqrt{(X_{C1} - X_P)^2 + (Y_P - Y_{C1})^2} \quad (20)$$

$$C_2 = \sqrt{(X_{C2} - X_P)^2 + (Y_P - Y_{C2})^2} \quad (21)$$

Referring now to FIG. 13, a perspective schematic view of a measurement device 300 having an inclinometer 476 is shown disposed within a vessel 100. FIG. 13 also includes the measurement values that may be used when determining vessel verticality. As explained above, the inclinometer measures the vessel verticality relative to a horizontal plane 1300. The inclinometer measures the tilt of the vessel 100 along the X-axis 1302 and Y-axis 1304 of the plane 1300. The measurement values that may be used when calculating vessel verticality include the following:

TABLE 4

Vessel Verticality Values

| Value | Description |
|---|---|
| $X_{AXIS}$ | X-axis direction tilt as indicated by the inclinometer |
| $Y_{AXIS}$ | Y-axis direction tilt as indicated by the inclinometer |
| $\Phi_X$ | angular offset of the vessel along the X-axis from a 0° horizontal plane as indicated by the inclinometer |

TABLE 4-continued

Vessel Verticality Values

| Value | Description |
|---|---|
| $\Phi_Y$ | angular offset of the vessel along the Y-axis from a 0° horizontal plane as indicated by the inclinometer |
| $\Theta_X$ | compensated X-axis direction tilt |
| $\Theta_Y$ | compensated Y-axis direction tilt |

During measurement of the vessel verticality, the measurement device 300 may first be calibrated to obtain initial angle offsets $\Phi_X$ and $\Phi_Y$. To calibrate the measurement device 300, the measurement device 300 may be placed on a 0° horizontal surface. Angle offsets $\Phi_X$ and $\Phi_Y$ are then measured using the inclinometer and stored. Inclinometer angles $\Theta_X$ and $\Theta_Y$ representing vessel verticality along the X-axis and Y-axis respectively may then be calculated using the angular offsets $\Phi_X$ and $\Phi_Y$ and the $X_{AXIS}$ and $Y_{AXIS}$ direction tilt readings from the inclinometer 476:

$$\Theta_X = X_{AXIS} + \Phi_X \quad (22)$$

$$\Theta_Y = Y_{AXIS} + \Phi_Y \quad (23)$$

Having obtained the shaft center position $(C_1, C_2)$ at the top and bottom of the shaft 110 respectively as well as the vessel verticality $(\Theta_X, \Theta_Y)$, the shaft verticality relative to the vessel may then be calculated.

Figure 14:
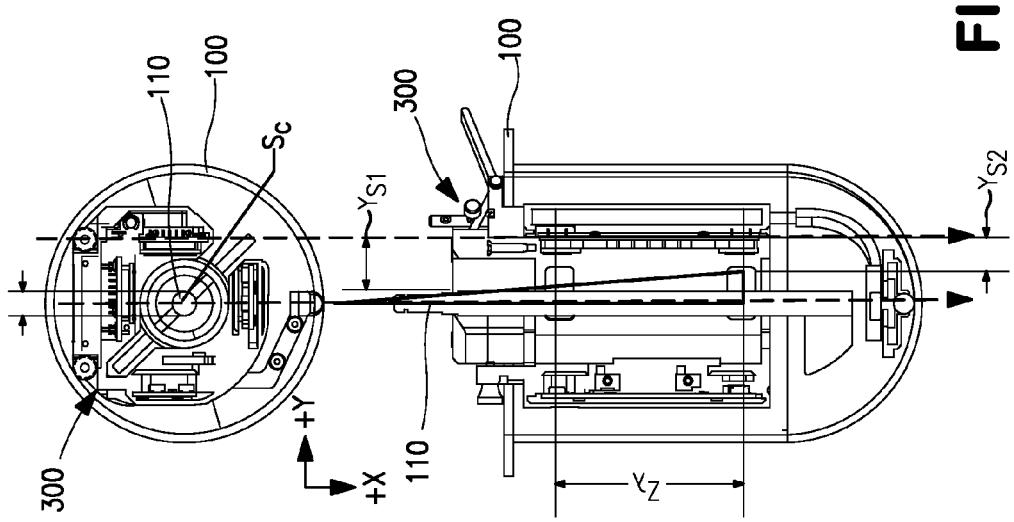
FIG. 14 is a top and a side schematic view of a shaft and a measurement device disposed within a vessel illustrating the measurements that may be used to calculate the verticality of the shaft.

With reference to FIG. 14, a top and side schematic view of a measurement device 300 and shaft 110 is shown disposed within a vessel 100. FIG. 14 also includes the measurement values that may be used when calculating shaft verticality relative to the vessel 100. The measurement values that may be used when calculating shaft verticality include the following:

TABLE 5

Shaft Verticality Values

| Value | Description |
|---|---|
| SC | shaft center |
| RP | reference point for the shaft center (SC) measured from the center of a contact point |
| $Z_\lambda$ | known vertical distance between the first pixel of an upper linear sensor array and the first pixel of a lower linear sensor array |
| $X_{\phi 1}$ | distance along the X-axis from the first pixel of the upper linear sensor array to the shaft edge |
| $Y_{\phi 1}$ | distance along the Y-axis from the first pixel of the upper linear sensor array to the shaft edge |
| $X_{\phi 2}$ | distance along the X-axis from the first pixel of the lower linear sensor array to the shaft edge |
| $Y_{\phi 2}$ | distance along the Y-axis from the first pixel of the lower linear sensor array to the shaft edge |
| $X_{S1}$ | distance between the reference point (RP) and the shaft edge along the X-axis at the top of the shaft |
| $Y_{S1}$ | distance between the reference point (RP) and the shaft edge along the Y-axis at the top of the shaft |
| $X_{S2}$ | distance between the reference point (RP) and the shaft edge along the X-axis at the bottom of the shaft |
| $Y_{S2}$ | distance between the reference point (RP) and the shaft edge along the Y-axis at the bottom of the shaft |
| $\Theta_X$ | vessel X-axis direction tilt |
| $\Theta_Y$ | vessel Y-axis direction tilt |
| $A_X$ | angular offset of the shaft relative to vertical along the X-axis |
| $A_Y$ | angular offset of the shaft relative to vertical along the Y-axis |

Using the equations set forth above, the following values may be obtained prior to calculating the shaft verticality: the distance along the X-axis and Y-axis $(X_{\phi 1}, Y_{\phi 1})$ and $(X_{\phi 2}, Y_{\phi 2})$ from the first pixel of the upper linear sensor array to the shaft edge at the top and bottom of the shaft 110; the distance along the X-axis and Y-axis $(X_{S1}, Y_{S1})$ and $(X_{S2}, Y_{S2})$ between the reference point RP and the shaft edge at the top and bottom of the shaft 110; and the vessel tilt $(\Theta_X, \Theta_Y)$ in the X-axis and Y-axis directions. Having calculated these values, the angular offset of the shaft 110 $(A_X, A_Y)$ along the X-axis and the Y-axis respectively may be calculated from the shaft edge positions and the vessel tilt in two directions that are 90° apart:

$$A_X = \arctan\left(\frac{(X_{S1} - X_{S2})}{Z_\lambda}\right) * \frac{180°}{\pi} + \Theta_X \quad (24)$$

$$A_Y = -\left(\arctan\left(\frac{(Y_{S1} - Y_{S2})}{Z_\lambda}\right) * \frac{180°}{\pi}\right) + \Theta_Y \quad (25)$$

Figure 15:
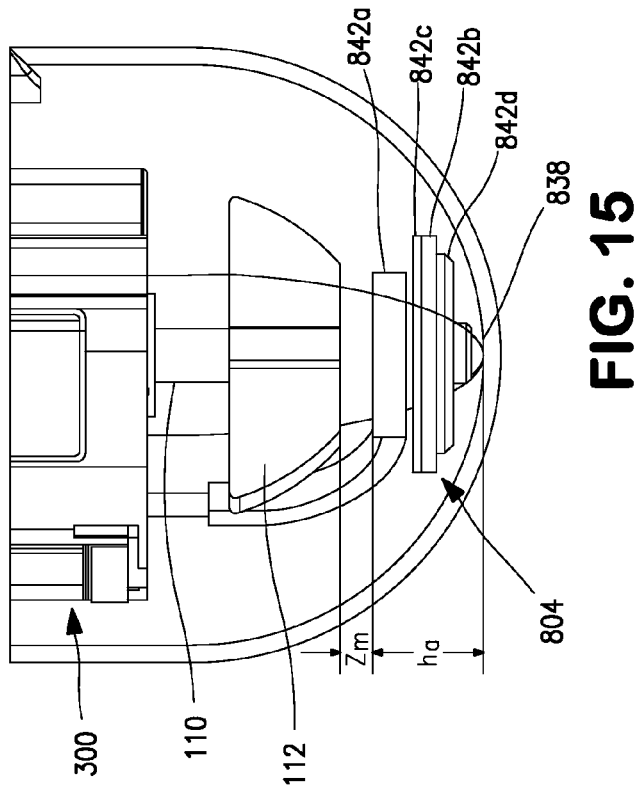
FIG. 15 is a side schematic view of a shaft and measurement device disposed within a vessel illustrating the measurements that may be used to calculate the distance from the bottom of the vessel to the bottom of a paddle or basket attached to the end of the shaft.

Referring now to FIG. 15, a side schematic view of a measurement device 300 and a shaft 110 are shown disposed within a vessel 100. FIG. 15 also includes the measurement values that may be used to calculate the height of a paddle 112 or basket above the bottom of the vessel 100. The measurement values that may be used when calculating paddle/basket height include:

TABLE 6

Paddle/Basket Height Values

| Value | Description |
|---|---|
| $H_A$ | known height of the target pad |
| $Z_\Delta$ | measured movement of the target pad from the bottom of the vessel to the bottom of the paddle/basket |
| $H_P$ | calculated height of the paddle/basket above the bottom of the vessel |

As seen in FIG. 15, the height $H_P$ of the paddle/basket 112 above the bottom of the vessel 100 is the sum of the height of the target pad 804 and the measured movement of the target pad 804 from the bottom of the vessel 100 to the bottom of the paddle/basket 112. As seen in FIG. 15, the height $H_A$ of the target pad 804 includes: the portion of the ball bearing 838 extending from the base 842d; the base 842d itself; the retaining ring 842b, the mounting cap 842c, and the housing cap 842a. The height $H_A$ may be measured prior to inserting the measurement device 300 into the vessel 100 using, for example, calipers. The height $H_A$ may then be stored in the measurement device 300 or the calculation unit for determining the height $H_P$ of the paddle/basket 112 from the bottom of the vessel 100. Knowing the height $H_A$ of the target pad 804, the distance $Z_\Delta$ to the bottom of the paddle/basket 112 may be measured according to the steps set forth in FIG. 9C above. Having obtained the measured distance $Z_\Delta$, the height $H_P$ of the paddle/basket 112 may be calculated with the following equation:

$$H_P = H_A + Z_\Delta \quad (26)$$

The measurements and values calculated above may also be used to calculate shaft wobble $W_S$ and basket wobble $W_B$ while the shaft is rotating in the vessel 100. For example, shaft wobble $W_B$ and basket wobble $W_B$ may be calculated by taking the difference of a minimum and maximum shaft position and basket position respectively during one or more revolutions of the shaft. Shaft wobble $W_S$ may be calculated using a lower pair of linear sensor arrays and basket wobble $W_B$ may be calculated using the upper pair of linear sensor arrays. The measurement values that may be used when calculating shaft wobble include:

TABLE 7

Shaft Wobble and Basket Wobble Values

| Value | Description |
|---|---|
| $X_{S1}$ | distance between the reference point (RP) and the shaft edge along the X-axis at the top of the shaft |
| $X_{S2}$ | distance between the reference point (RP) and the shaft edge along the X-axis at the bottom of the shaft |
| $Z_1$ | value obtained from the linear encoder of the height gauge system |
| SR | data stream rate |
| RPM | rotational speed |
| P | points per set |
| T | duration of the testing period |
| $W_S$ | shaft wobble along the X-axis using the lower pair of linear sensor arrays |
| $W_B$ | shaft wobble along the X-axis using the upper pair of linear sensor arrays |

When calculating shaft wobble, the distance $X_{S2}$ between the reference point RP and the shaft edge along the X-axis at the bottom of the shaft 110 may first be calculated according to the equations set forth above. The data stream rate SR may be, for example, 4 Hertz (Hz), 2 Hz, 1 Hz, or 0.5 Hz. A typical data stream rate SR may be, for example, 4 Hz. Shaft wobble may be calculated as the difference of the minimum and maximum shaft edge position readings over a test period T, such as 5 seconds. Having calculated the distance $X_{S2}$, the shaft wobble may be calculated using the following equations:

$$P = T * SR \tag{27}$$

$$W_S = \underset{i=1}{\overset{i=P}{\text{Max}}}(X_{S2}[i]) - \underset{i=1}{\overset{i=P}{\text{Min}}}(X_{S2}[i]) \tag{28}$$

Similarly, having raised the basket upwards to align with the upper pair of linear sensor arrays as described with reference to FIG. 9G and having calculated the distance $X_{S1}$, basket wobble $W_B$ may be calculated using the following equation:

$$W_B = \underset{i=1}{\overset{i=P}{\text{Max}}}(X_{S1}[i]) - \underset{i=1}{\overset{i=P}{\text{Min}}}(X_{S1}[i]) \tag{29}$$

Alternatively, basket wobble $W_B$ may be calculated via the height gauge system 304 and the basket wobble lifter 306 (FIG. 3). To measure basket wobble $W_B$ using this alternative method, the basket is raised upwards and positioned adjacent the pad 848 (FIGS. 8A-B) of the basket wobble lifter 306. As explained above, the pad 848 is spring-biased towards the basket, and wobble of the basket while the shaft 110 is rotating will push the pad and the lifter portion 858 towards the upper plunger rod 818b causing vertical movement of the upper plunger rod 818b. The linear encoder 482b senses this vertical movement and generates signals corresponding to the position of the upper plunger rod 818b as the upper plunger rod 818b moves up and down. The signals from the linear encoder 482b may then be used to calculate basket wobble while the shaft 110 rotates. Basket wobble $W_B$ may be calculated using this alternative method with the following equation(s):

$$W_B = \underset{i=1}{\overset{i=P}{\text{Max}}}(Z_1[i]) - \underset{i=1}{\overset{i=P}{\text{Min}}}(Z_1[i]) \tag{30}$$

Figure 16:
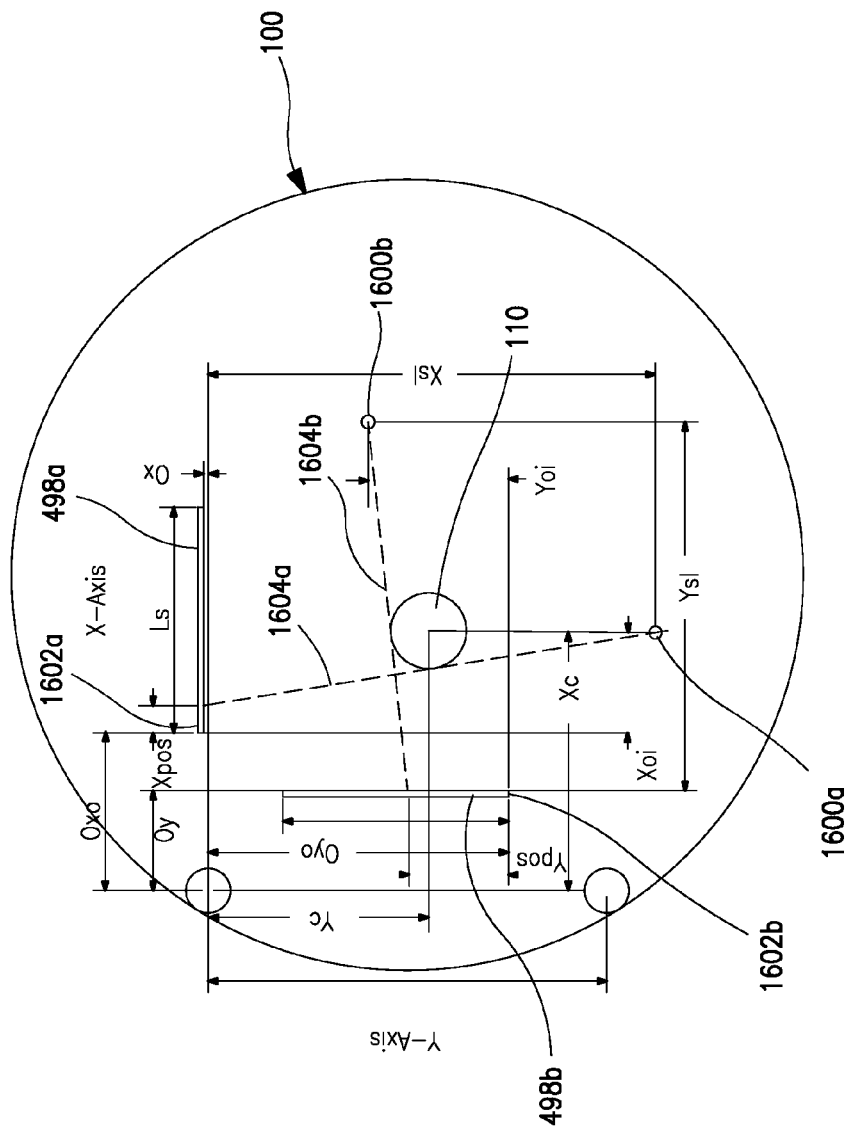
FIG. 16 is a top schematic view of a shaft and a measurement device having a single point light source disposed within a vessel illustrating the measurements that may be used to calculate the center of the shaft.

Referring now to FIG. 16, a top schematic view of an alternative embodiment of the measurement device 300 having a single point light source 1600a-b for each light emitting component 486a-b as described above. As seen in FIG. 16 a shaft 110 is shown disposed within a vessel 100. FIG. 16 also includes the measurement values that may be used when calculating shaft center using a measurement device 300 having a single point light source 1600. The measurement values that may be used when calculating shaft center in the alternative embodiment include the following:

TABLE 8

Alternative Shaft Center Values

| Value | Description |
|---|---|
| SC | shaft center |
| RP | reference point for the shaft center (SC) measured from the center of a contact point |
| $D_S$ | shaft diameter |
| $R_S$ | shaft radius |
| $O_X$ | known distance along Y-axis from reference point (RP) to X-axis sensor |
| $O_Y$ | known distance along X-axis from reference point (RP) to Y-axis sensor |
| $O_{X0}$ | known distance along X-axis from reference point (RP) to the first pixel in the X-axis sensor |
| $O_{Y0}$ | known distance along Y-axis from reference point (RP) to the first pixel in the Y-axis sensor |
| $X_{SL}$ | known distance along Y-axis from X-axis sensor to corresponding light source |
| $Y_{SL}$ | known distance along X-axis from Y-axis sensor to corresponding light source |
| $X_{0I}$ | known distance along X-axis from first pixel in X-axis sensor to center of corresponding light source |
| $Y_{0I}$ | known distance along Y-axis from first pixel in Y-axis sensor to center of corresponding light source |
| $S_L$ | sensor length |
| $X_{POS}$ | measured reading from X-axis sensor representing distance along X-axis from first pixel in X-axis sensor to first light-activated pixel |
| $Y_{POS}$ | measured reading from Y-axis sensor representing distance along Y-axis from first pixel in Y-axis sensor to first light-activated pixel |
| $X_{X1}$ | calculated distance along X-axis from reference point (RP) to center of light source for X-axis sensor |
| $X_{Y1}$ | calculated distance along Y-axis from reference point (RP) to center of light source for X-axis sensor |
| $Y_{X1}$ | calculated distance along X-axis from reference point (RP) to center of light source for Y-axis sensor |
| $Y_{Y1}$ | calculated distance along Y-axis from reference point (RP) to center of light source for Y-axis sensor |
| $X_{X2}$ | calculated distance along X-axis from reference point (RP) to first light-activated pixel in X-axis sensor |
| $X_{Y2}$ | calculated distance along Y-axis from reference point (RP) to first light-activated pixel in X-axis sensor |
| $Y_{X2}$ | calculated distance along X-axis from reference point (RP) to first light-activated pixel in Y-axis sensor |
| $Y_{Y2}$ | calculated distance along Y-axis from reference point (RP) to first light-activated pixel in Y-axis sensor |
| $M_X$ | calculated slope of line between light source for X-axis sensor and first light-activated pixel of X-axis sensor |
| $M_Y$ | calculated slope of line between light source for Y-axis sensor and first light-activated pixel of Y-axis sensor |
| $B_X$ | calculated intersection with the Y-axis of the line between light source for X-axis sensor and first light-activated pixel of X-axis sensor |

TABLE 8-continued

Alternative Shaft Center Values

| Value | Description |
|---|---|
| $B_Y$ | calculated intersection with the Y-axis of the line between light source for Y-axis sensor and first light-activated pixel of Y-axis sensor and the Y-axis |
| $M_{X\,PERP}$ | calculated slope of the line perpendicular to the line $M_X$ |
| $M_{Y\,PERP}$ | calculated slope of the line perpendicular to the line $M_Y$ |
| $X_{X3}$ | calculated distance along the X-axis from the reference point (RP) to the intersection point of the line $M_{X\_PERP}$ and the line parallel to the line $M_X$ passing through the center of the shaft |
| $X_{Y3}$ | calculated distance along the Y-axis from the reference point (RP) to the intersection point of the line $M_{X\_PERP}$ and the line parallel to the line $M_X$ passing through the center of the shaft |
| $B_{XC}$ | calculated intersection with the Y-axis of the line parallel to the line $M_X$ passing through the center of the shaft |
| $Y_{X3}$ | calculated distance along the X-axis from the reference point (RP) to the intersection point of the line $M_{Y\_PERP}$ and the line parallel to the line $M_Y$ passing through the center of the shaft |
| $Y_{Y3}$ | calculated distance along the Y-axis from the reference point (RP) to the intersection point of the line $M_{Y\_PERP}$ and the line parallel to the line $M_Y$ passing through the center of the shaft |
| $B_{YC}$ | calculated intersection with the Y-axis of the line parallel to the line $M_Y$ passing through the center of the shaft |
| $X_C$ | calculated distance along the X-axis from the reference point RP to the shaft center (SC) |
| $Y_C$ | calculated distance along the Y-axis from the reference point RP to the shaft center (SC) |

When calculating the shaft center SC using the alternative embodiment of the measurement device 300, some values relating arrangement of the device components may be known values measured or determined prior to measuring the position of a shaft 110 within a vessel 100. These known values may then be stored in the measurement device 300 as constants and used when calculating the position of the shaft center SC in the vessel 100. For example, known constants may include: the shaft diameter $D_S$ and shaft radius $R_S$; the distance $O_X$ and $O_Y$ between the reference point RP and the sensor 498a parallel to the X-axis and the sensor 498b parallel to the Y-axis respectively; the distance $O_{X0}$ and $O_{Y0}$ along the X-axis and Y-axis respectively between the reference point RP and the first pixel in the sensors 498a-b; the distance $X_{SL}$, and $Y_{SL}$ from the X-axis sensor 498a along the Y-axis to its corresponding light source 1600a and from the Y-axis sensor 498b along the X-axis to its corresponding light source 1600b respectively; the distance $X_{OI}$ and $Y_{OI}$ from the first pixel in the X-axis sensor 498a along the X-axis to the center of its corresponding light source 1600a and from the Y-axis sensor 498b along the Y-axis to the center of its corresponding light source 1600b respectively.

Further, certain values may be measured before the location of a shaft 110 is calculated. For example, the measurement device 300 may measure and store the distance $X_{POS}$ and $Y_{POS}$ along the X-axis and Y-axis respectively from the first pixel 1602a in the X-axis sensor 498a to the first light-activated pixel of the X-axis sensor 498a and from the first pixel 1602b in the Y-axis sensor 498b to the first light-activated pixel of the Y-axis sensor 498b. From these known values, the center of the shaft 110 may be calculated with the equations set forth below.

Using the known and measured values described above, the position $(X_{X1}, X_{Y1})$ and $(Y_{X1}, Y_{Y1})$ of the center of the light source 1600a-b respectively may be calculated with the following equations:

$$X_{X1}=O_{XO}+X_{OI} \quad (31)$$

$$X_{Y1}=O_X-X_{SL} \quad (32)$$

$$Y_{X1}=O_Y+Y_{SL} \quad (33)$$

$$Y_{Y1}=O_{YO}+Y_{OI} \quad (34)$$

Additionally, the known values may be used to calculate the position $(X_{X2}, X_{Y2})$ and $(Y_{X2}, Y_{Y2})$ of the first activated pixels 1602a-b in the X-axis sensor 498a and the Y-axis sensor 498b respectively using the following equations:

$$X_{X2}=O_{XO}+X_{POS} \quad (35)$$

$$X_{Y2}=O_X \quad (36)$$

$$Y_{X2}=O_Y \quad (37)$$

$$Y_{Y2}=O_{YO}+Y_{POS} \quad (38)$$

Having calculated the positions of the light sources 1600a-b and the positions of the first activated pixel 1602a-b in each sensor 498a-b, the slopes $M_X$, $M_Y$ of the lines 1604a-b respectively representing the beam of light between the light source 1600a-b and the corresponding sensor 498a-b may be calculated using the following equations:

$$M_X=(X_{Y2}-X_{Y1})/(X_{X2}-X_{X1}) \quad (39)$$

$$M_Y=(Y_{Y2}-Y_{Y1})/(Y_{X2}-Y_{X1}) \quad (40)$$

The slopes $M_X$, $M_Y$ may then be used to calculate the Y-axis intercepts $B_X$, $B_Y$ of the lines 1604a-b respectively using the formula for a line:

$$B_X=X_{Y1}-(M_X*X_{X1}) \quad (41)$$

$$B_Y=Y_{Y1}-(M_Y*Y_{X1}) \quad (42)$$

The slopes $M_X$, $M_Y$ may also be used to calculate the slope of the lines $M_{X\_PERP}$, $M_{Y\_PERP}$ perpendicular to the lines 1604a-b representing the beams of light from the single point light sources 1600a-b:

$$M_{X\_PERP} = \frac{-1}{M_X} \quad (43)$$

$$M_{Y\_PERP} = \frac{-1}{M_Y} \quad (44)$$

Next, the intersection point of the line $(X_{X3}, X_{Y3})$ parallel to line $M_X$ and perpendicular to $M_{X\_PERP}$ and passing through the center of the shaft 110 and the Y-intercept $B_{XC}$ of the line parallel to line $M_X$ and perpendicular to $M_{X\_PERP}$ and passing through the center of the shaft 110 for the X-axis sensor 498a may be calculated with the following equations:

$$X_{X3} = \sqrt{R_S^2 / \left(1 + \left(\frac{1}{M_X}\right)^2\right)} \quad (45)$$

$$X_{Y3} = B_X + (M_{X\_PERP} * X_{X3}) \quad (46)$$

$$B_{XC} = X_{Y3} - (M_X * X_{X3}) \quad (47)$$

Similarly, the intersection point of the line $(Y_{X3}, Y_{Y3})$ parallel to line $M_Y$ and perpendicular to $M_{Y\_PERP}$ and passing through the center of the shaft 110 and the Y-intercept $B_{YC}$ of the line parallel to line $M_Y$ and perpendicular to $M_{Y\_PERP}$ and passing through the center of the shaft 110 for the Y-axis sensor 498$b$ may be calculated with the following equations:

$$Y_{X3} = \sqrt{R_S^2 / \left(1 + \left(\frac{1}{M_Y}\right)^2\right)} \quad (48)$$

$$Y_{Y3} = B_Y + (M_{Y\_PERP} * Y_{X3}) \quad (49)$$

$$B_{YC} = Y_{Y3} - (M_Y * Y_{X3}) \quad (50)$$

Finally, the location of the center of the shaft ($X_C$, $Y_C$) may be determined using the following equations:

$$X_C = (B_{XC} - B_{YC})/M_Y - M_X \quad (51)$$

$$Y_C = B_{XC} + (M_X * X_C) \quad (52)$$

Those skilled in the art will understand that these equations represent an alternative method of calculating the position of the center of the shaft 110 where the measurement device 300 has, for example, a single point light source. These equations may be used for calculating the center of an upper portion of the shaft 110 as measured from an upper pair of sensors as well as the center of a lower portion of the shaft 110 with a lower pair of sensors. Further, those skilled in the art will understand that having obtained the position of the center of the shaft 110, the equations with reference to shaft center offset and shaft verticality may also be used with embodiments having a single point light source.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. An apparatus for determining at least one parameter relating to a position of an elongate member disposed within a vessel, the apparatus comprising:
   at least one measurement unit comprising a light emitting component and a corresponding light receiving component, the light receiving component positioned apart from the light emitting component such that the elongate member is positionable between the light emitting component and the light receiving component;
   the light emitting component configured for emitting light towards the light receiving component; and
   the light receiving component configured for generating a signal corresponding to the light received from the light emitting component, the signal corresponding to light received from the light emitting component indicating the at least one parameter relating to the position of the elongate member disposed within the vessel.

2. The apparatus of claim 1, further comprising:
   a calculation unit configured to receive the signal generated by the light receiving component and to determine the at least one parameter based on the received signal.

3. The apparatus of claim 2, wherein the calculation unit is configured for determining at least one of:
   (a) a location of the elongate member relative to a vertical axis of the vessel;
   (b) an angular position of the elongate member relative to the vertical axis of the vessel;
   (c) a deviation of the elongate member from the vertical axis of the vessel during an operative mode; and
   d) a deviation of an agitator attached to a lower end of the elongate member during an operative mode.

4. The apparatus of claim 1, wherein the at least one measurement unit further comprises:
   a first measurement unit having a first light emitting component and a first light receiving component; and
   a second measurement unit having a second light emitting component and a second light receiving component, the second measurement unit being positioned substantially co-planar with and at an angle relative to the first measurement unit;
   wherein light emitted from the first light emitting component towards the first light receiving, component intersects light emitted from the second light emitting component towards the second light receiving component.

5. The apparatus of claim 1, further comprising:
   a first filter positioned adjacent the light emitting component such that light emitted from the light emitting component passes through the first filter; and
   a second filter positioned adjacent the light receiving component such that light of a preselected wavelength range passes through the second filter and is received by the light receiving component.

6. The apparatus of claim 1, wherein the light emitting component comprises at least one light emitting diode and wherein the light receiving component comprises a linear sensor array.

7. The apparatus of claim 1, wherein the at least one measurement unit is an optical micrometer.

8. The apparatus of claim 1, wherein the at least one measurement unit further comprises;
   a first pair of measurement units positioned substantially co-planar with and at an angle relative to each other; and
   a second pair of measurement units positioned below the first pair of measurement units, the second pair of measurement units positioned substantially co-planar with and at an angle relative to each other.

9. The apparatus of claim 1, further comprising:
   a spring; and
   a laterally displaceable arm attached to the spring, the laterally displaceable arm configured to secure the apparatus within the vessel in response to the spring biasing the arm towards an interior side wall of the vessel.

10. The apparatus of claim 9, further comprising:
    a securing component that secures the laterally displaceable arm in an inwardly displaced position while the spring is compressed.

11. The apparatus of claim 9, further comprising:
    a transducer adapted to sense a lateral displacement of the laterally displaceable arm and generate signals corresponding to a position of the laterally displaceable arm.

12. The apparatus of claim 1, further comprising:
    a linearly displaceable arm for determining a distance from a lower end of the elongate member to a bottom of the vessel;
    a pad attached to an end of the linearly displaceable arm, the pad positioned proximate the bottom of the vessel below the lower end of the elongate member;
    a bearing secured within the pad; and
    a transducer configured for sensing a linear displacement of the linearly displaceable arm and generate signals corresponding to a position of the linearly displaceable arm.

13. The apparatus of claim 1, further comprising:
    a rotational speed indicator configured for determining a rotational speed of the elongate member during an operative mode, the rotational speed indicator having a magnet secured within a mounting component mountable to the elongate member; and a transducer configured for sensing rotation of the elongate member based on the position of the magnet and to generate signals corresponding to the rotation of the elongate member.

14. The apparatus of claim 1, further comprising:
an inclinometer configured for sensing an angular position of the vessel relative to one or more axes and to generate signals corresponding to the angular position of the vessel.

15. The apparatus of claim 1, wherein the at least one measurement unit is installed in the vessel.

16. A method for determining at least one parameter relating to an elongate member disposed within a vessel, the method comprising:
obtaining measurements relating to the elongate member disposed within the vessel with an apparatus positioned within the vessel, wherein the apparatus is spaced apart from the elongate member;
illuminating the elongate member with light emitted from a light emitting component of the apparatus such that the light is emitted towards the elongate member and received by a light receiving component of the apparatus positioned apart from the light emitting component, and the light receiving component generates a signal corresponding to the light received from the light emitting component; and
calculating, based on the signal generated by the light emitting component, at least one of a location of the elongate member relative to a vertical axis of the vessel, and an angular position of the elongate member relative to a vertical axis of the vessel.

17. The method of claim 16, further comprising:
initiating a rotation of the elongate member; and
calculating, based on the signal generated by the light emitting component, at least one of a deviation of the elongate member from the vertical axis of the vessel, and a deviation of an agitator attached to a lower end of the elongate member from the vertical axis of the vessel.

18. The method of claim 16, further comprising:
raising a linearly displaceable arm towards a lower end of the elongate member, the linearly displaceable arm having a pad attached to an end of the linearly displaceable arm;
releasing the linearly displaceable arm such that a transducer senses the position of the linearly displaceable arm and generates signals corresponding to the position of the linearly displaceable arm; and
calculating a distance between the lower end of the elongate member and a bottom of the vessel based on the signals generated by the transducer.

19. The method of claim 16, further comprising:
initiating a rotation of the elongate member such that a sensor senses a rotational position of the elongate member based on the position of a rotational speed indicator;
generating signals corresponding to the rotational position of the elongate member; and
calculating a rotational speed of the elongate member based on the signals generated by the sensor.

20. The method of claim 16, further comprising:
measuring a position of the vessel relative to one or more axes such that an inclinometer senses the position of the vessel and generates signals corresponding to the position of the vessel; and
calculating an angular position of the vessel based on signals received from the inclinometer.

* * * * *